US008058401B2

(12) United States Patent
Schofield

(10) Patent No.: US 8,058,401 B2
(45) Date of Patent: Nov. 15, 2011

(54) IMMUNOGENIC COMPOSITIONS AND USES THEREOF

(75) Inventor: Louis Schofield, Gisborne (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 0 days.

(21) Appl. No.: 12/501,859

(22) Filed: Jul. 13, 2009

(65) Prior Publication Data

US 2009/0275737 A1 Nov. 5, 2009

Related U.S. Application Data

(62) Division of application No. 09/787,111, filed as application No. PCT/AU99/00770 on Sep. 14, 1999, now Pat. No. 7,575,755.

(30) Foreign Application Priority Data

Sep. 14, 1998 (AU) .................................. PP5893/98

(51) Int. Cl.
*A61K 38/00* (2006.01)
*A61K 39/00* (2006.01)
*C07K 16/00* (2006.01)
*C12P 21/08* (2006.01)

(52) U.S. Cl. ............... 530/387.1; 530/387.5; 530/388.6; 514/1.1; 424/178.1

(58) Field of Classification Search ........................ None
See application file for complete search history.

(56) References Cited

U.S. PATENT DOCUMENTS

| 5,726,166 | A | 3/1998 | Playfair et al. ................. 514/129 |
| 5,968,742 | A | 10/1999 | Bandman et al. |
| 6,113,917 | A | 9/2000 | Fasel et al. ................... 424/268.1 |
| 6,551,586 | B1 | 4/2003 | Davidson et al. |
| 7,575,755 | B1 * | 8/2009 | Schofield ..................... 424/268.1 |
| 7,928,077 | B2 * | 4/2011 | Wong et al. ...................... 514/25 |
| 7,932,361 | B2 * | 4/2011 | Ruben et al. ................. 530/387.9 |
| 7,968,689 | B2 * | 6/2011 | Rosen et al. ................. 530/387.9 |
| 2005/0169935 | A1 * | 8/2005 | Aylsworth et al. .......... 424/185.1 |
| 2006/0089330 | A1 | 4/2006 | Seeberger et al. .............. 514/54 |
| 2006/0147476 | A1 * | 7/2006 | Schofield .................... 424/268.1 |
| 2008/0044428 | A1 | 2/2008 | Schofield .................... 424/172.1 |
| 2009/0275737 | A1 * | 11/2009 | Schofield .................... 530/389.1 |

FOREIGN PATENT DOCUMENTS

| AU | 65674/94 | | 12/1994 |
| DE | 4311580 | | 8/1994 |
| EP | 1113815 A1 * | | 7/2001 |
| EP | 1545599 A1 * | | 6/2005 |
| WO | WO 97/10249 | | 3/1997 |
| WO | WO 00/24406 | | 5/2000 |
| WO | WO 00/24406 A1 * | | 5/2000 |
| WO | WO 2004/0011026 A1 | | 2/2004 |
| WO | WO 2005/120519 A1 | | 12/2005 |

OTHER PUBLICATIONS

Riley et al, Parasite Immunology, 2006, 28:35-49.*
Greenspan et al, Nature Biotechnology 17:936-937, 1999.*
Harlow et al In Antibodies A Laboratory Manual, Cold Spring Harbor Press, 1988, Chapter 3, pp. 23-35.*
Greenbaum et al, Journal of Molecular Recognition, 20(2):75-82, 2007.*
Herbert, Dictionary of Immunology 4th Ed, Academic Press, 1995 pp. 58-59.*
Gerold et al., "Structual analysis of the glycosyl-phosphatidylinositol membrane anchor of the merozoite surface proteins-1 and -2 of *Plasmodium falciparum*," *Molecular and Biochemical Parasitology* (1996), vol. 75, pp. 131-143, Elsevier Science B.V.
Schofield et al., "Neutralizing monoclonal antiboides to glycosylphosphatidylinositol, the dominant TNF-a-inducing toxin of *Plasmodium falciparum*: prospects for the immunotherapy of severe malaria," *Annals of Tropical Medicine and Parasitology* (1993), vol. 87, No. 6, pp. 617-626, Liverpool School of Tropical Medicine.
Richardson et al., "Native and baculovirus-expressed forms of the immuno-protective protein BM86 from *Boophilus microplus* are anchored to the cell membrane by a glycosyl-phosphatidyl inositol linkage," *Insect Molecular Biology* (1993), vol. 1, No. 3, pp. 139-147.
Schofield et al., "Regulation of host cell function by glycosylphosphatidylinositols of the parasitic protozoa," *Immunology and Cell Biology* (1996), vol. 74, pp. 555-563.
Scholfield et al., "Signal Transduction in Host Cells by a Glycosylphosphatidylinositol Toxin of Malaria Parasites," *J. Exp. Med.* (Jan. 1993), vol. 177, pp. 145-153, The Rockefeller University Press.
Tachado et al., "Signal transduction in macrophages by glycosylphosphatidylinositols of Plasmodium, Trypanosoma, and Leishmania: Activation of protein tyrosine kinases and protein kinase C by inositolglycan and diacylglycerol moieties," *Proc. Natl. Acad. Sci.* (Apr. 1997), vol. 94, pp. 4022-4027, The National Academy of Sciences of the USA.
Reymond et al., "Anchoring of an Immunogenic *Plasmodium falciparum* Circumsporozoite Protein on the Surface of *Dictyostelium discoideum*," *The Journal of Biological Chemistry* (1995), vol. 270, No. 21, pp. 12941-12947.
Schofield et al., "Signal transduction in host cells mediated by glycosylphosphatidylinositols of the parasitic protozoa, or why do the parasitic protozoa have so many GPI molecules?," *Brazilian J. Med. Biol. Res.* (1994), vol. 27, pp. 249-254.
McConville et al., "The structure, biosynthesis and function of glycosylated phosphatidylinositols in the parasitic protozoa and higher eukaryotes," *Biochem. J.* (1993), vol. 294, pp. 305-324, Great Britain.

(Continued)

*Primary Examiner* — Nita M Minnifield
(74) *Attorney, Agent, or Firm* — Scully, Scott, Murphy & Presser, P.C.

(57) ABSTRACT

The present invention relates generally to a method of eliciting or otherwise inducing an effective immune response to a micro-organism and compositions for use therein. More particularly, the present invention relates to a method of inducing an immune response to a parasite utilising an immunogenic composition comprising a glycosylphosphatidylinositol (referred to herein as "GPI") inositolglycan domain or its derivatives. Even more particularly, the present invention contemplates an immunogenic composition comprising the *Plasmodium falciparum* GPI inositolglycan domain or its derivatives. The present invention is useful, inter alia, as a prophylactic and/or therapeutic treatment for disease conditions such as, for example, infection by parasites and in particular infection by *Plasmodium* species.

8 Claims, 12 Drawing Sheets

OTHER PUBLICATIONS

Elhay et al., "Lipophosphoglycan expression and virulence in Ricin-resistant variants of *Leishmania major*," *Molecular and Biochemical Parasitology* (1990), vol. 40, pp. 255-268, Elsevier Scinece Publishers B.V. (Biomedical Division).
Misek et al., "An Inositol Phosphate Glycan Derived from a *Trypanosome brucei* Glycosyl-Phosphatidylinositol Mimics some of the Metabolic Actions of Insulin," *The Journal of Biological Chemistry* (Aug. 15, 1992), vol. 267, No, 23, pp. 16266-16273, The American Society for Biochemistry and Molecular Biology, Inc.
Romero G. et al., "Anti-inositolglycan antibodies selectively block some of the actions of insulin in intact $BC_3H1$ cells," *Proc. Natl. Acas. Sci. USA 87*:1476-1480 (1990).
Schenkman S. et al., "Glycophosphatidylinositol-anchored proteins inmetacyclic trypomastigotes of *Trypanosoma cruzi", Molecular and Biochemical Parasitology 29*:141-152 (1988).
Galili U., "Evolution and pathophysiology of the human natural anti-α-galactosyl IgG (anti-Gal) antibody", *Sprigner Semin Immunopathol* 15:155-171 (1993).
Dumitriu, S., "Polysaccharides in Medicinal Applications", Marcel Dekker, Inc. pp. 277-291 (1996).
Gowda et al., Parasitology Today, 1999, 15/4: 147-152.
Ramasamy, BBA, 1998, 1406: 10-27.
Clark at al., Parasitology Today, 2000, 16/10: 451-454.
Gowda, Microbes and Infection, 2002, 4:983-990.
Robert et al., Current Opinion in Microbiology, 2000, 3:395-403.
Butikofer et al., FASEBJ, 2001, 15:545-548.
Schofield et al., J. Immunology 156: 1886-1896, 1996.
Tachado at al., PNAS, USA, 94: 4022-4027, 1997.
Richardson et al., Insect Molecular Biology, vol. 1(issue 3): 139-147, 1993.
Tachado et al., J. Immunology 156: 1897-1907, 1996.
Fujita et al., BBA, Mar. 2008, 1780/3:410-420, Abstract only.
Debierre-Grockiego et al., Infection and Immunity, Oct. 2006, 74/10:5487-5496.
Streipen et al., J. Mol. Biol., 1997, 266: 797-813.
Paulick et al., J. Am. Chem. Soc., 2007, 129: 11543-11550.
Sauma et al., Molecular and Biochemical Parasitology 38: 199-210, 1990.
Tiede et al., Biol. Chem. 380: 503-523, 1999.
Gazzinelli et al., Ciencia e Cultura 51(5/6): 411-428, 1999.
Kedees et al., European J. Cell Biology 79: 52-61, 2000.
Schofield et al., Science, 283: 225-229, 1999.
Tachado et al., Parasite Immunology 21: 609-617, 1999.
Garg et al., JBC, 272/19: 12482-12491, 1997.
Zunecker et al., Indian J. biochemistry and Biophysics, 34: 105-109, 1997.
Tachado et al., BRRC 205/2: 984-991, 1994.
Eckert et al., European J. Cell Biol. 69/Suppl 42: 148, Abstract #443, 1996.
Moran et al., JCB, 125/2: 333-343, 1994.
Schofield et at, Nature 418: 785-789, 2002.
Campos et al., J. Immunology, 167: 416-423, 2001.
Delorenzi et al., Infection and Immunity 70/8: 4510-4522, 2002.
Schofield, In: Parotysmal Nocturnal Hemoglobineria and the Glycosylphosphatidylinasitol-linked proteins, Editor Young et al., pp. 179-198, 2000.
Azzouz et al., Glycobiology, 10/2: 177-183, 2000.
Fanning et al., Vaccine, 2003, 21:3228-3235.
Clark et al., Pharmacology and Therapetuics, 2003, 99: 221-260.
Dekker, et al., Molecular and Biochemical Parasitology, 2004, 137: 143-149.
Lu et al., Tetrahedron Letters, 2004, 45: 879-882.
Bruna Romero et al., Vaccine, 2004, 22: 3575-3584.
Glaser, Current Opinion in Structural Biology, 1993, ¾: 475-481, Abstract only.

* cited by examiner

IMMUNOGENIC COMPOSITIONS AND USES THEREOF

CROSS-REFERENCE TO RELATED APPLICATIONS

This application is a divisional application of U.S. Ser. No. 09/787,111, filed on May 14, 2001, now U.S. Pat. No. 7,575,755 B1, issued on Aug. 18, 2009, which is the §371 national phase of International Application No. PCT/AU99/00770, filed on Sep. 14, 1999.

FIELD OF THE INVENTION

The present invention relates generally to a method of eliciting or otherwise inducing an immune response to a micro-organism and compositions for use therein. More particularly, the present invention relates to a method of inducing an immune response to a parasite utilising an immunogenic composition comprising a glycosylphosphatidylinositol (referred to herein as "GPI") inositolglycan domain or its derivative or equivalent. The present invention is useful, inter alia, as a prophylactic and/or therapeutic treatment for micro-organism infections of mammals such as, for example, parasite infections and in particular infection by Plasmodium species.

BACKGROUND OF THE INVENTION

Bibliographic details of the publications numerically referred to in this specification are collected at the end of the description.

The malaria parasite is considered to be one of the single most serious infectious agents in the world, infecting 5% of the global population and causing serious mortality and morbidity to sensitive populations and hampering socioeconomic development.

Severe malaria infection shares several clinical features in common with bacterial septic shock. In both conditions, the excess production by macrophages of pro-inflammatory cytokines such as Tumor Necrosis Factor (TNF), Interleukin-1 (IL-1) and IL-6 occurs in response to malaria "toxins" and lipopolysaccharide (LPS), respectively, leading to complications such as fever and hyperpyrexia, leukopenia, thrombocytopenia, hypotension, disseminated intravascular coagulation, leukocyte infiltration, vascular permeability and multi-organ inflammation, which may lead eventually to death. Thus, many signs, symptoms and syndromes in acute and severe malaria infection result from the activity of a parasite "toxin" released into the circulation during the blood-stage developmental cycle of the infection.

GPI has been identified as a candidate toxin of parasite origin (Schofield and Hackett, 1993 and Tachado et al, 1997). The structure of the molecule has been elucidated (Gerold et al, 1992 and Gerold et al, 1996) and it comprises a lipidic domain and a glycan domain. Intact GPI occurs in two closely related forms, Pfglα (NH—$CH_2$—$CH_2$—$PO_4$-(Manα1-2)-6Manα1-2Manα1-6Manα1-4GlcN—$H_2$α1-6(myristoyl)-myo-Inositol-1-$PO_4$-dipalmitoylglycerol), and Pfglβ (NH—$CH_2$—$CH_2$—$PO_4$-6Manα1-2Manα1-6Manα1,4GlcN—$H_2$α1-6(myristoyl)-myo-Inositol-1-$PO_4$-dipalmitoylglycerol).

The parasite derived GPI molecule regulates host cell function and gene expression in various tissues by activating endogenous GPI-based signal transduction pathways, involving hydrolysis into second messengers and the activation of both tyrosine and serine/threonine kinases. This leads to the activation of the NFκB/c-rel family of transcription factors, which regulate the expression of numerous pro-inflammatory loci implicated in malarial pathology, such as TN-F IL-1, iNOS and ICAM-1.

The toxin theory of malarial pathogenesis can be ascribed to Camillo Golgi, in 1886, who hypothesized that the proximal cause of the febrile paroxysm was a released toxin of parasite origin (Golgi, 1886). Clark proposed that the systemic inflammation of malaria infection resulted from a functional malarial endotoxin, and suggested that this agent exerts systemic effects largely through the induction of endogenous pyrogens of host origin. Clark correctly identified TNF as a major host mediator of disease (Clark, 1978 and Clark et al, 1981). Consequently, the production of this and related pyrogenic cytokines (IL-1, IL-6) from monocyte/macrophages is often taken as a useful surrogate marker for the initiation of pathological processes in malaria infection. John Playfair and his colleagues extended this work to show that crude extracts of rodent malaria parasites could induce macrophages to secrete TNF in vitro (Bate et al, 1988 and Bate et al, 1989) and inferred that the toxin included a phospholipid moiety. Nonetheless, prior to the advent of the present invention, the specific biochemical identity of the parasite toxin, and its mechanism of action, have remained obscure.

In work leading up to the present invention, the inventors investigated the use of portions of GPI to induce protective immunity against malarial pathology. The inventors have surprisingly discovered that GPI portions which exclude the lipidic domain induce protective immunity whereas portions carrying the lipidic domain do not.

SUMMARY OF THE INVENTION

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention is directed to a method of eliciting or inducing, in a mammal, an immune response directed to a micro-organism said method comprising administering to said mammal an effective amount of an immunogenic composition which composition comprises a molecule capable of inducing an immune response directed to the inositolglycan domain of a GPI but which molecule is substantially incapable of inducing an immune response directed to a lipidic domain of said GPI.

Another aspect of the present invention provides a method of eliciting or inducing, in a mammal, an immune response directed to a micro-organism said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain.

Still another aspect of the present invention is directed to a method of eliciting or inducing, in a mammal, an immune response directed to a parasite said method comprising administering to said mammal an effective amount of an immunogenic composition which composition comprises the inositolglycan domain portion of a parasite GPI or derivative or equivalent thereof and which inositolglycan domain portion comprises insufficient lipidic domain of said parasite GPI to induce or elicit an immune response directed to said lipidic domain.

Still yet another aspect of the present invention contemplates a method of eliciting or inducing, in a mammal, an immune response directed to *P. falciparum* said method comprising administering to said mammal an effective amount of an immunogenic composition which composition comprises a GPI inositolglycan domain wherein said GPI inositolglycan domain comprises the structure ethanolamine-phosphate-(Manα1,2)-Manα1,2Manα1, 6Manα1,4GlcN-myo-inositol phosphoglycerol or derivative or equivalent thereof.

Still yet another aspect of the present invention contemplates a method of eliciting or inducing, in a mammal, an immune response directed to *P. falciparum* said method comprising administering to said mammal an effective amount of an immunogenic composition which composition comprises a GPI inositolglycan domain wherein said GPI inositolglycan domain comprises the structure $X_1$-$X_2$-$X_3$-$X_4$-ethanolamine-phosphate-(Manα1,2)-Manα1,2Manα1,6Manα1,4GlcN-myo-inositol phosphoglycerol wherein $X_1$, $X_2$, $X_3$ and $X_4$ are any 4 amino acids, or derivative or equivalent of said GPI inositolglycan domain.

Still yet another aspect of the present invention contemplates a method of eliciting or inducing, in a mammal, an immune response directed to *P. falciparum* said method comprising administering to said mammal an effective amount of an immunogenic composition which composition comprises a GPI inositolglycan domain wherein said GPI inositolglycan domain comprises the structure EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EltN-P]Mα2 Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[Mα2][G]Mα2 M
EtN-P-[Mα2][X]Mα2 M
EtN-P-[Mα2][EtN-P]Mα2 M or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

A further aspect of the present invention contemplates a method of therapeutically or prophylactically treating a mammal for a micro-organism infection said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with infection of said mammal by said micro-organism.

Another further aspect of the present invention is directed to a method of therapeutically or prophylactically treating a mammal for a micro-organism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with infection of said mammal by said micro-organism.

In a related aspect, the present invention provides a method for the treatment and/or prophylaxis of a mammalian disease condition characterised by a micro-organism infection, said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with said micro-organism infection.

Still another further aspect of the present invention is directed to a method for the treatment and/or prophylaxis of a mammalian disease condition characterised by a micro-organism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with said micro-organism infection.

Still yet another aspect of the present invention relates to the use of a composition comprising a molecule capable of inducing an immune response directed to a micro-organism GPI inositolglycan domain but substantially incapable of inducing an immune response directed to a lipidic domain of GPI in the manufacture of a medicament for the therapeutic and/or prophylactic treatment of a mammalian disease condition characterised by infection with said micro-organism.

Still yet another further aspect of the present invention relates to the use of an immunogenic composition comprising a *Plasmodium* GPI inositolglycan domain or derivative or equivalent thereof which inositolglycan domain comprises insufficient lipidic domain of a *Plasmodium* GPI to elicit or induce an immune response directed to a GPI lipidic domain in the manufacture of a medicament for the therapeutic and/or prophylactic treatment of a mammalian disease condition characterised by infection with said *Plasmodium*.

Another aspect of the present invention is directed to a composition capable of inducing an immune response directed to a micro-organism, said composition comprising a molecule capable of inducing an immune response against a micro-organism GPI inositolglycan domain but substantially incapable of inducing an immune response to a lipidic domain of a GPI.

Still another aspect of the present invention is directed to a composition capable of inducing an immune response directed to a micro-organism said composition comprising a modified GPI molecule or derivative or equivalent thereof which modified GPI molecule comprises insufficient lipidic domain to induce or elicit an immune response directed to a GPI lipidic domain.

Yet another aspect of the present invention relates to a vaccine composition comprising as the active component a molecule capable of inducing an immune response directed to a micro-organism GPI inositolglycan domain but substantially incapable of inducing an immune response directed to a lipidic do-main of a GPI, as broadly described above, together with one or more pharmaceutically acceptable carriers and/or diluents.

Still yet another aspect of the present invention relates to a vaccine composition comprising as the active component a modified GPI molecule or derivative or equivalent thereof which modified GPI molecule or derivative or equivalent thereof which modified GPI molecule comprises insufficient lipidic domain to induce or elicit an immune response directed to a GPI lipidic domain.

Still another aspect of the present invention is directed to a pharmaceutical composition comprising a molecule capable of inducing an immune response directed to a micro-organism GPI inositolglycan domain but substantially incapable of inducing an immune response directed to a lipidic domain of a GPI, as broadly described above, together with one or more pharmaceutically acceptable carriers and/or diluents.

A further aspect of the present invention is directed to antibodies to GPI inositolglycan domains but substantially incapable of interacting with the lipidic domain of a GPI.

Yet another aspect of the present invention relates to a pharmaceutical composition comprising an antibody directed to a GPI inositolglycan domain together with one or more pharmaceutically acceptable carriers or diluents as hereinbefore described.

A further aspect of the present invention relates to the use of the antibodies of the present invention in relation to disease conditions. For example, the present invention is particularly useful but in no way limited to use in treating parasitic infections, their symptoms and pathologies.

Another aspect of the present invention relates to a method of inhibiting, halting or delaying the onset of progression of a mammalian disease condition characterised by a micro-organism infection said method comprising administering to said mammal an effective amount of an antibody has hereinbefore described.

In yet another aspect the present invention relates to the use of an antibody in the manufacture of a medicament for inhibiting, halting or delaying the onset or progression of a disease condition characterised by the infection of a mammal by a microorganism.

DETAILED DESCRIPTION OF THE INVENTION

Figure 1:
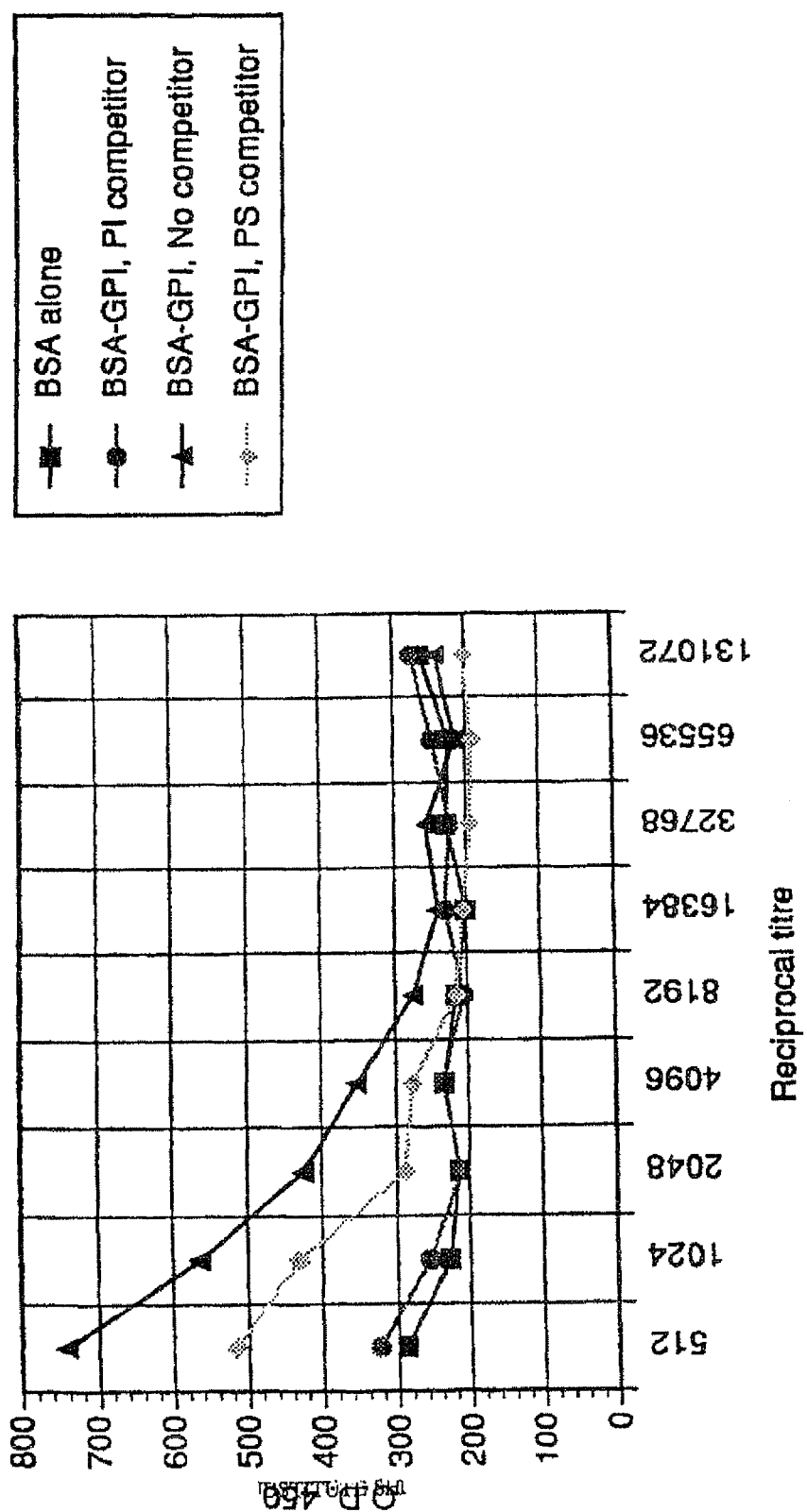
FIG. 1 is a graphical representation of the epitope specificity of anti-GPI antibodies determined by competition ELISA. Sera from mice immunized with free GPI were screened for reactivity to malarial GPI in the presence or absence of defined competitors (Phosphatidylinositol or phosphatidylserine).

The present invention is predicated, in part, on the surprising determination that a *Plasmodium* GPI molecule which excludes the lipidic portion will induce protective immunity whereas a GPI molecule which comprises the lipidic domain will not. This determination has facilitated the development of compositions and methodology for application, inter alia, in the prophylactic or therapeutic treatment of micro-organism infection.

Accordingly, one aspect of the present invention is directed to a method of eliciting or inducing, in a mammal, an immune response directed to a micro-organism said method comprising administering to said mammal an effective amount of an immunogenic composition which composition comprises a molecule capable of inducing an immune response directed to the inositolglycan domain of a GPI but which molecule is substantially incapable of inducing an immune response directed to a lipidic domain of said GPI.

The present invention is predicated on the surprising observation that mice immunised with purified, intact, free GPI mount an IgM dominated response directed predominantly to the lipidic domain of the molecule, which cross reacts with host GPI lipidic domains which are exposed at host cell surfaces. The antibodies are not protective clinically against subsequent parasite infection. In fact, passive transfer of these antibodies exacerbates disease severity. However, immunisation with the glycan domain of malarial GPI results in IgG antibodies interactive with the glycan domain of GPI and mice thus immunised are substantially protected against pathology induced by subsequent malaria challenge. Passive transfer of these IgG antibodies is protective against pathology. The inventors have demonstrated, therefore, that IgM antibodies to the lipidic domain and IgG antibodies to the glycan domain of the malaria GPI differ in their effects, the former promoting disease and the latter preventing it. It should be understood that in preventing or minimising the induction of an immune response directed to the GPI of a micro-organism, the onset of an immune response directed to lipidic domain of the subject mammal (host) is thereby prevented or minimised by virtue of minimising the production of antibodies to a micro-organism GPI which would otherwise cross react with the host GPI.

GPIs are ubiquitous among eukaryotes, described from *T. brucei*, *T. cruzi*, *Plasmodium*, *Leishmania*, and *Toxoplasma*, as well as yeast, insect, fish and numerous mammalian sources (for recent reviews see McConville and Ferguson, 1993 and Stevens, 1995). GPIs consist of a conserved core glycan (Man$\alpha$1-2Man$\alpha$1-6Man$\alpha$1-4GlcNH$_2$) linked to the 6-position of the myo-inositol ring of phosphatidylinositol (PI). GPIs are built up on the cytoplasmic face of the endoplasmic reticulum (ER) by the sequential addition of sugar residues to PI by the action of glycosyltransferases. The maturing GPI is then translocated across the membrane to the luminal side of the ER, whence it may be exported to the cell surface, free or in covalent association with proteins. The tetrasaccharide core glycan may be further substituted with sugars, phosphates and ethanolamine groups in a species and tissue-specific manner. GPI fatty acid moieties can be either diacylglycerols, alkylacylglycerols, monoalkylglycerols or ceramides, with additional palmitoylations or myristoylations to the inositol ring. The overall picture is of a closely related family of glycolipids sharing certain core features but with a high level of variation in fatty acid composition and side-chain modifications to the conserved core glycan.

Accordingly, reference herein to "GPI inositolglycan domains" should be read as including reference to all forms of GPI inositolglycan domains and derivatives or equivalents thereof. The term "GPI inositolglycan" is used interchangeably with terms such as but not limited to "inositolglycan" (IG), "inositophosphoglycan" (IPG), "phosphoinositolglycan" (PIG), "phosphooligosaccharide" (POS) and the molecules described by these terms should be understood as "GPI inositolglycan" molecules. It should also be understood that reference to "GPI inositolglycan domain" includes reference to a GPI inositolglycan domain linked, bound or otherwise associated with non-inositolglycan molecules such as, but not limited to, the glycerol linker sequence which links the lipidic domain to the inositolglycan domain, a non-immunogenic portion of the lipidic domain or an amino acid peptide.

Preferably the molecule is a portion of GPI which comprises the inositolglycan domain or derivative or equivalent thereof but substantially does not contain a portion capable of inducing an immune response directed to a lipidic domain of said GPI.

Accordingly, the present invention more particularly provides a method of eliciting or inducing, in a mammal, an immune response directed to a micro-organism said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain.

Preferably, said modified GPI molecule is the inositolglycan domain portion of GPI or derivative or equivalent thereof.

Still without limiting the present invention in any way, the administration of an immunogenic composition comprising an inositolglycan domain portion of GPI or derivative or equivalent thereof substantially lacking the lipidic domain, as hereinbefore defined, is also thought to benefit the subject mammal by minimizing certain unwanted responses which may otherwise occur incidentally to immune response induction, but which enhance disease severity, if the subject immunogenic molecule comprised a lipid domain. Specifically;

(i) the intact GPI is a toxin and may induce non-immunological physiological sensitization in recipients such that the response to the natural GPI toxin is exacerbated upon malaria challenge. The inventors have shown that the lipidic portion of the intact GPI is necessary for full toxic activity by virtue of its' ability to initiate lipid-dependent signaling in host cells, and act as a lipidic second messenger;

(ii) intact glycolipids may associate with host CD1 molecules for presentation to CD1-restricted NKT cells or other unusual T cell lineages. These T cells are known to produce high levels of cytokines such as interferon-$\gamma$ and IL-4 very rapidly in response to stimulation and are likely to be crucial regulators of downstream TH1/TH2 differentiation. Immunization with purified, intact (i.e. lipidated), free GPI may result in priming of these T cells which subsequently respond with high levels of interferon-$\gamma$ upon parasite challenge, thereby exacerbating the disease syndromes. That is, immunological sensitization of unusual T cells may contribute to the phenomenon of exacerbated disease severity.

"Derivatives" and "equivalents" should be understood to include fragments, parts, portions, chemical equivalents, mutants, homologs and analogs. Chemical equivalents of a GPI inositolglycan domain can act as a functional analog of the GPI inositolglycan domain. For example, a chemical equivalent of the GPI inositolglycan domain includes a GPI inositolglycan domain in which the phosphoglycerol component of the inositolglycan has been modified to increase hydrophobicity. This may be achieved by replacement with truncated, partial or modified fatty acids or other hydrophobic moieties and acts to improve the immunogenicity or stability of the molecule, without generating an undesirable antibody response. Chemical equivalents may not necessarily be derived from a GPI inositolglycan domain but may share certain confirmational similarities. Alternatively, chemical equivalents may be specifically designed to mimic certain immunological and physiochemical properties of the GPI inositolglycan domain. Chemical equivalents may be chemically synthesised or may be detected following, for example, natural product screening. Chemical equivalents also include synthetic carbohydrates and peptide mimics. Homologs of GPI inositolglycan domains contemplated herein include, but are not limited to, GPI inositolglycan domains from different species including, for example, *Saccharomyces*. Fragments, include portions such as the glycan component of the inositolglycan domain, which portions are effective in achieving the object of the present invention.

GPI inositolglycan domains suitable for use in the present invention may be derived from any natural, recombinant or synthetic source. This includes, for example, GPI inositolglycan domains derived by genetic manipulation of expression systems, and by manipulations of the GPI post-translational modifications of proteins via recombinant DNA techniques such as glycosylation inhibitors. It also includes chemically synthetic or semi-synthetic inositolglycan domains and fragments thereof derived by any chemical process including the use of enzymes for the addition or removal of residues.

The term "micro-organism" should be understood in its broadest sense and includes, for example, the parasitic and fungal taxa *Plasmodium, Trypanosoma, Leishmania, Toxoplasma* and *Candida*. "Micro-organism" should also be understood to extend to molecules which are secreted by or shed from the subject organism. This would include for example, toxin molecules or molecules which are cleared from the surface of the micro-organism. Preferably, the GPI inositolglycan domain suitable for use in the present invention is a parasite GPI inositolglycan domain and even more preferably a *Plasmodium* GPI inositolglycan domain.

Accordingly, the present invention is preferably directed to a method of eliciting or inducing, in a mammal, an immune response directed to a parasite said method comprising administering to said mammal an effective amount of an immunogenic composition which composition comprises the inositolglycan domain portion of a parasite GPI or derivative or equivalent thereof and which inositolglycan domain portion comprises insufficient lipidic domain of said parasite GPI to induce or elicit an immune response directed to said lipidic domain.

Even more preferably said parasite GPI inositolglycan domain is a *Plasmodium* GPI inositolglycan domain or derivative or equivalent thereof.

Most preferably, said *Plasmodium* is *P. falciparum*.

Yet even more preferably, the present invention contemplates a method of eliciting or inducing, in a mammal, an immune response directed to *P. falciparum* said method comprising administering to said mammal an effective amount of an immunogenic composition which composition comprises a GPI inositolglycan domain wherein said GPI inositolglycan domain comprises the structure
  ethanolaminie-phosphate-(Manα1,2)-Manα1,2Manα1,
    6Manα1,4GlcN-myo-inositol phosphoglycerol
or derivative or equivalent thereof.

In another most preferred embodiment the immunogenic composition comprises a GPI inositolglycan domain wherein said GPI inositolglycan domain comprises the structure
  $X_1$-$X_2$-$X_3$-$X_4$-ethanolamine-phosphate-(Manα1,2)-
    Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment the immunogenic composition comprises a GPI inositolglycan domain wherein said GPI inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
EtN-P-Mα2 Mα6 Mα4G
Mα2 Mα6 Mα4G
EtN-P-Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
Mα2 [Mα2][G]Mα2 Mα6 Mα4G
Mα2 [Mα2][X]Mα2 Mα6 Mα4G
Mα2 [Mα2][EtN-P]Mα6 Mα4G
or derivative or equivalent thereof wherein EtN is ethanolamine, P is phosphate, M is mannose, C is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
or derivative or equivalent thereof wherein EtN is ethanolamine, P is phosphate, M is mannose, G is non-N-acetylated glucosaminie, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
EtN-P-[Mα2][G]Mα2 Mα6 M
EtN-P-[Mα2][X]Mα2 Mα6 M
EtN-P-[Mα2][EtN-P]Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a CPI inositolglycan domain wherein said GPI inositolglycan domain comprises a structure selected from:
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the immunogenic composition comprises a GPI inositolglycan domain wherein said GPI inositolglycan domain comprises a structure selected from:
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolaminie, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

Any of these structures may be further modified by substituents of positive, negative or neutral charge such as phosphates, phosphoglycerol, hexosamines, amino acids, thiols etc in any position and with any type of linkage. These structures may be further modified by addition of any number of amino acids for the purpose of providing a linkage sequence.

It should be understood that non-N-acetylated hexosamine includes glucosamine or any other nitrous-acid labile substituent. It should be further understood that any of these structures may be further modified by substituents including, but not limited to, of positive, negative or neutral charge such as phosphates, phosphoglycerol, hexosamines, amino acids or thiols in any position and with any type of linkage.

The GPI inositolglycan domain of the present invention may be conjugated to another molecule. Said conjugation may be performed for any one or more reasons such as, but not limited to:
(i) The GPI inositolglycan domain may be too small to be antigenic. Accordingly, conjugation to a carrier molecule, such as a protein, may be required such that said GPI inositolglycan domain, which forms part of the GPI inositolglycan domain-conjugate, acts as a hapten and immunity is induced to said GPI inositolglycan domain. The carrier protein may be selected from a range of antigenic proteins such as but not limited to recombinant proteins derived from *Plasmodium* gene sequences, tetanus toxoid, purified protein derivative, hepatitis B or Key Hole Limpet Haemocyanin and Diptheria toxoid.
(ii) The GPI inositolglycan domain when conjugated with specific anti-pathogen vaccine molecules (such as anti-malarial vaccine molecules) may result in the production of anti-inositolglycan domain antibodies which reverse the immune suppression that otherwise may occur in response to exposure to the native form of the vaccine molecule where said molecule is itself GPI-anchored. For example, the GPI inositolglycan domain may be coupled to a malarial recombinant protein which can act as both a carrier protein and a vaccine in its own right. Without intending to limit this aspect of the present invention to any one theory or mode of action, primary and secondary T lymphocyte responses to some GPI-anchored surface protein antigens are inhibited by the GPI anchor. Examples of such protein antigens includes Circumsporozoite (CS) proteins of *P. falciparum* and *P. berghei* and the membrane-form of Variant Surface Glycoprotein of *T. brucei*. Since immunisation against synthetic or recombinant peptides or proteins of GPI-anchored surface molecules such as the CS protein, MSP-1, MSP-2 or MSP-4, for example, may be insufficient to allow MHC Class II anamnestic boosting when the native antigens are encountered during natural parasitic challenge due to the induction of immunosuppression, immunisation against the GPI moiety provides a means to alleviate this immunosuppression.
(iii) The GPI inositolglycan domain may comprise only part of the target epitope. For example, peptide sequences, other carbohydrates (and any associated post-translational modifications) corresponding to C-terminal domains of native GPI-anchored proteins or GPI-anchored glycosconjugates may also form part of the target GPI inositolglycan domain epitope. Removal of any part of the epitope (by removing the portion of the C-terminal domain which forms part of the GPI inositolglycan domain epitope) may lead to reduction or loss of binding of antibodies. Said peptide sequences or carbohydrates would therefore be conjugated to said GPI inositolglycan domain. For example, some antibodies to malarial GPI, while specifically neutralising GPI function, recognise epitopes which predominantly include the inositolglycan but also include portions of the protein to which the GPIs are actually bound in nature, i.e. the adjacent C-terminal portions of GPI-anchored proteins. The presence of peptide domains can also improve the affinity of certain antibodies, for example by helping to stabilise the inositolglycan conformationally. Furthermore, such conjugation can render a relatively unimmunogenic inositolglycan domain sufficiently immunogenic. Specifically, the inclusion of a C-terminal peptide determinant, for example, may help increase the immunogenicity of the inositolglyean by forming a composite antigen which is more immunologically foreign than inositolglycan alone.

The resulting GPI inositolglycan domain-conjugate may be administered as a preparation formulated in or with an adjuvant. The adjuvant is selected from the range of adjuvants known to induce high levels of antibody, including water in oil emulsions, oil in water emulsions, water in oil in water double emulsions, saponin, Quil A extracts and other derivatives of saponin, DEAE-dextran, dextran sulphate, aluminium salts and nonionic block co-polymers. The adjuvant may include other immunomodulators, such as muramyl-dipeptide and derivatives, cytokines, and cell wall components from species of mycobacteria or corynebacteria. The adjuvant formulation may include a combination of two or more of the adjuvants listed. These lists are not to be taken as exhaustive. The selection of adjuvant is in part dependent on the species being targeted and is based on the level and duration of the immune response required and on the lack of reactogenicity (ie tissue compatibility). The level of active component and adjuvant are chosen to achieve the desired level and duration of immune response.

Host GPIs play a significant role in the normal physiological regulation of various cellular responses in higher eukaryotes. Foreign GPIs such as GPIs of parasite origin exert pathophysiological effects, and specifically regulate host cell function, by acting as a mimic of endogenous host GPI signalling pathways. Signal transduction induced in host cells by GPI's of *P. falciparum*, *T. brucei*, and *L. mexicana*, for example, activate the macrophage lineage-specific hck member of the src-family of protein tyrosine kinases within 30 seconds of addition to cells (Tachado et al, 1997). Protein tyrosine kinase (PTK) activation is required for downstream gene expression resulting in phosphorylation, cell signalling and TNF, IL-1, iNOS, ICAM-1 and VCAM expression (Schofield et al, 1996, Tachado et al, 1996 and Tachado et at, 1997). PTK activation maps to the inositolglycan moiety of GPI and follows binding of the core glycan to a receptor on the surface of cells (Tachado et al, 1997). Parasite GPIs appear to activate similar kinases as those activated upon perturbation of endogenous GPI-anchored proteins at the cell surface.

The toxic nature of foreign GPIs such as parasite GPIs can be exemplified with respect to malarial GPIs. When inoculated in vivo, the malarial GPI induces pyrexia and symptoms of acute malaria and causes the death of the recipient in a standard assay of TNF driven lethality (Schofield and Hackett, 1993). In addition to inducing TNF and IL-1 expression in macrophages, the GPI exerts several other TNF independent effects on host tissues that may contribute to pathological processes in malaria infections. GPI directly increases expression of E-selectin, ICAM and VCAM in vascular endothelial cells (Schofield et al, 1996). GPI also induces de novo protein synthesis of inducable nitric oxide synthase and the production of NO in a time and dose dependent manner, from macrophages and synergises with interferon-$\gamma$ in this activity (Tachado et al, 1996). In the hypoxic or ischaemic model, cerebral malaria is proposed to result from a blockage of the post capillary venules of the brain by sequestered parasite infected erythrocytes binding to the adhesion molecules ICAM, VCAM and E-selectin (Berendt et al, 1994). GPI can therefore be lethal in vivo and induce malarial symptomology encompassing both systemic inflammation and organ-specific pathology such as the cerebral syndrome.

Foreign GPIs may also induce immunosuppression. GPIs isolated from *P. falciparum* and *T. brucei*, for example, when added at low concentrations to cultures of CD4+ and CD8+ $\alpha/\beta$ TCR+T cells block cell cycle progression and cellular proliferation, inhibiting the upregulation of IL-2 R/CD25 and CD28 expression and blocking expression of IL-2, interferon $\gamma$, and IL-4. The GPIs also inhibit the T cell proliferative response to IL-2. In vivo, GPI anchored surface proteins such as malaria CS protein, MSP-1, MSP-2, and the membrane form variant surface glycoprotein of *T. brucei* inhibit, via the covalently associated GPI anchor, primary and secondary T lymphocyte responses to said antigens.

While not intending to limit the present invention to any one theory or mode of action, immunisation with a GPI molecule lacking the lipid domain induces an IgG response to the inositolglycan domain which blocks subsequent parasitic GPI action. Both toxicity and immunosuppression, as described above, are significantly reduced.

A further aspect of the present invention relates to the use of the invention in relation to disease conditions. For example, the present invention is particularly useful, but in no way limited to use in therapeutically or prophylactically treating parasitic infections such as by immunizing a mammal against a parasitic infection. In this regard, it should be understood that the method of the present invention is directed to inducing an immune response for the purpose of alleviating or preventing the onset of symptoms associated with a parasitic infection (such as toxicity and immunosuppression) and/or where the GPI domain is conjugated to a suitable antipathogen molecule, reducing or preventing parasitic infection. Reference herein to "symptoms" associated with a micro-organism infection should be understood to extend to both the infection itself as well as the physical and/or physiological consequences (such as toxicity or immunosuppresion) of such an infection.

Accordingly, another aspect of the present invention contemplates a method of therapeutically or prophylactically treating a mammal for a micro-organism infection said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with infection of said mammal by said micro-organism.

More particularly, the present invention is directed to a method of therapeutically or prophylactically treating a mammal for a micro-organism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with infection of said mammal by said micro-organism.

Preferably, said micro-organism is a parasite and even more preferably *Plasmodium falciparum*.

In accordance with this preferred aspect of the present invention, the immunogenic composition preferably comprises a GPI inositolglycan domain wherein said GPI inositolglycan domain comprises the structure ethanolamine-phosphate-(Man$\alpha$1,2)-Man$\alpha$1,2Man$\alpha$1,6Man$\alpha$1,4GlcN-myo-inositol phosphoglycerol or derivative or equivalent thereof.

In another preferred embodiment, the subject inositolglycan domain comprises the structure X$_1$-X$_2$-X$_3$-X$_4$-ethanolamine-phosphate-(Manα1,2)-Manα1,2Manα1,6Manα1,4GlcN-myo-inositol phosphoglycerol wherein X$_1$, X$_2$, X$_3$ and X$_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-Mα2 Mα6 Mα4G
Mα2 Mα6 Mα4G
EtN-P-Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglyean domain comprises a structure selected from:
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
or derivative or equivalent thereof wherein EtN is ethanolamine, P is phosphate, M is mannose, G is non-N-acetylated glucosamnie, [C] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 Mα4G
Mα2 [Mα2][X]Mα2 Mα6 Mα4C
Mα2 [Mα2][EtN-P]Mα6 Mα4G
or derivative or equivalent thereof wherein EtN is ethanolamine, P is phosphate, M is mannose, G is non-N-acetylated glucosaminie, [C] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 M
EtN-P-[Mα2][X]Mα2 Mα6 M
EtN-P-[Mα2][EtN-P]Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4C
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, C is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

The term "mammal" includes humans, primates, livestock animals (eg. horses, cattle, sheep, pigs, donkeys), laboratory test animals (eg. mice, rats, rabbits, guinea pigs), companion animals (eg. dogs, cats) and captive wild animals (eg. kangaroos, deer, foxes). Preferably, the mammal is a human or laboratory test animal. Even more preferably, the mammal is a human.

The mammal undergoing treatment may be a human or animal in need of therapeutic or prophylactic treatment for a disease condition or a potential disease condition.

Without limiting this aspect of the present invention, administration of said immunogenic composition may act to result in production of antibodies which either prevent manifestation of symptoms such as toxicity and immunosuppression or which affect the parasite directly, for example, by killing the parasite via binding to its surface and inhibiting its growth, development or the onward progression of the overall infection.

An "effective amount" means an amount necessary at least partly to attain the desired immune response, or to prevent or to delay the onset or inhibit progression or halt altogether, the onset or progression of a particular condition being treated. This amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of onset of a particular condition. "Treatment" may also reduce the severity of an existing condition or the frequency of acute attacks (for example, reducing the severity of initial infection).

In accordance with these methods, the modulatory agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules, These molecules may be administered in any order.

In a related aspect, the present invention provides a method for the treatment and/or prophylaxis of a mammalian disease condition characterised by a micro-organism infection, said method comprising administering to said mammal an effective amount of an immunogenic composition which composition comprises a molecule capable of inducing an immune response directed to the inositolglycan domain of a GPI, but substantially incapable of inducing an immune response directed to the lipid domain of a GPI, for a time and under conditions sufficient for said immune response to reduce, inhibit or otherwise alleviate any one or more symptoms associated with said micro-organism infection.

More particularly, the present invention is directed to a method for the treatment and/or prophylaxis of a mammalian disease condition characterised by a micro-organism infection said method comprising administering to said mammal an effective amount of an immunogenic composition which composition comprises a modified GPI molecule or derivative or equivalent thereof and which modified GPI molecule comprises insufficient lipidic domain to induce or elicit an immune response directed to a GPI lipidic domain for a time and under conditions sufficient for said immune response to reduce, inhibit or otherwise alleviate any one or more symptoms associated with said micro-organism infection.

Preferably, said disease condition is malaria and said micro-organism is *Plasmodium falciparum*.

In accordance with this preferred aspect of the present invention, the immunogenic composition preferably comprises a GPI inositolglycan domain wherein said GPI inositolglycan domain comprises the structure ethanolamine-phosphate-(Manα1,2)-Manα1,2Manα1,6Manα1,4GlcN-myo-inositol phosphoglycerol or derivative or equivalent thereof.

In another preferred embodiment, the subject inositolglycan domain comprises the structure $X_1$-$X_2$-$X_3$-$X_4$-ethanolamine-phosphate-(Manα1,2)-Manα1,2Manα1,6Manα1,4GlcN-myo-inositol phosphoglycerol wherein $X_1$, $X_2$, $X_3$ and $X_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-Mα2 Mα6 Mα4G
Mα2 Mα6 Mα4G
EtN-P-Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
or derivative or equivalent thereof wherein EtN is ethanolamine, P is phosphate, M is mannose, G is non-N-acetylated glucosaminie, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 Mα4G
Mα2 [Mα2][X]Mα2 Mα6 Mα4G
Mα2 [Mα2][EtN-P]Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 M
EtN-P-[Mα2][X]Mα2 Mα6 M
EtN-P-[Mα2][EtN-P]Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosplioglycerol, [X] is any other substituent, α represents α-linkages which may be substituted with β-linkages wherever required, and numeric values represent positional linkages which may be substituted with any other positional linkages as required.

In yet another aspect the present invention relates to the use of a composition comprising a molecule capable of inducing an immune response directed to a micro-organism GPI inositolglycan domain but substantially incapable of inducing an immune response directed to a lipidic domain of GPI in the manufacture of a medicament for the therapeutic and/or prophylactic treatment of a mammalian disease condition characterised by infection with said micro-organism.

Accordingly, another aspect the present invention relates to the use of an immunogenic composition comprising a *Plasmodium* GPI inositolglycan domain or derivative or equivalent thereof which inositolglycan domain comprises insufficient lipidic domain of a *Plasmodium* GPI to elicit or induce an immune response directed to a GPI lipidic domain in the manufacture of a medicament for the therapeutic and/or prophylactic treatment of a mammalian disease condition characterised by infection with said *Plasmodium*.

Preferably said disease condition is malaria.

The present invention should also be understood to extend to immunogenic compositions for use in the methods as hereinbefore defined.

Accordingly, in a related aspect, the present invention is directed to a composition capable of inducing an immune response directed to a micro-organism, said composition comprising a molecule capable of inducing an immune response against a micro-organism GPI inositolglycan domain but substantially incapable of inducing an immune response to a lipidic domain of a GPI.

More particularly, the present invention is directed to a composition capable of inducing an immune response directed to a micro-organism said composition comprising a modified GPI molecule or derivative or equivalent thereof which modified GPI molecule comprises insufficient lipidic domain to induce or elicit an immune response directed to a GPI lipidic domain.

Preferably, said modified GPI molecule is the inositolglycan domain portion of GPI.

Even more preferably, said micro-organism is a parasite and said parasite is *Plasmodium*.

In accordance with this preferred aspect of the present invention, the immunogenic composition preferably comprises a GPI inositolglycan domain wherein said GPI inositolglycan domain comprises the structure
ethanolamine-phosphate-(Manα1,2)-Manα1,2Manα1, 6Manα1,4GlcN-myo-inositol phosphoglycerol
or derivative or equivalent thereof.

In another preferred embodiment, the subject inositolglycan domain comprises the structure
$X_1$-$X_2$-$X_3$-$X_4$-ethanolamine-phosphate-(Manα1,2)-Manα1,2Manα1,6Manα1,4GlcN-myo-inositol phosphoglycerol
wherein $X_1$, $X_2$, $X_3$ and $X_4$ are any 4 amino acids, or derivative or equivalent of said GPI inositolglycan domain.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-Mα2 Mα6 Mα4G
Mα2 Mα6 Mα4G
EtN-P-Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment the subject inositolglycan domain comprises a structure selected from:
Mα2 [Mα2][G]Mα2 Mα6 Mα4G
Mα2 [Mα2][X]Mα2 Mα6 Mα6G
Mα2 [Mα2][EtN-P]Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent; α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 M
EtN-P-[Mα2][X]Mα2 Mα6 M
EtN-P-[Mα2][EtN-P]Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 M
Mα2 [Mα2][X]Mα2 Mα6 M
Mα2 [Mα2][EtN-P]Mα2 Mα6 M
Mα2 Mα6 M
Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

Yet another aspect of the present invention relates to a vaccine composition comprising as the active component a molecule capable of inducing an immune response directed to a micro-organism GPI inositolglycan domain but substantially incapable of inducing an immune response directed to a lipidic domain of a GPI, as broadly described above, together with one or more pharmaceutically acceptable carriers and/or diluents.

More particularly, the present invention relates to a vaccine composition comprising as the active component a modified GPI molecule or derivative or equivalent thereof which modified GPI molecule or derivative or equivalent thereof which modified GPI molecule comprises insufficient lipidic domain to induce or elicit an immune response directed to a GPI lipidic domain.

Preferably said modified GPI molecule is a GPI inositoglycan domain.

More preferably, said GPI inositolglycan domain is a parasite GPI inositolglycan domain and even more preferably a *Plasmodium* GPI inositolglycan domain.

Most preferably, said *Plasmodium* is *P. falciparum*.

In a most preferred embodiment, said molecule is a GPI inositolglycan domain comprising the structure
ethanolamine-phosphate-(Manα1,2)-Manα1,2Manα1, 6Manα1,4GlcN-phosphatidyl-myo-inositol phosphoglycerol.

In another most preferred embodiment said molecule is a GPI inositolglycan domain comprising the structure
$X_1$-$X_2$-$X_3$-$X_4$-ethanolamine-phosphate-(Manα1,2)-Manα1,2Manα1,6Manα1,4GlcN-myo-inositol phosphoglycerol
wherein $X_1$, $X_2$, $X_3$, $X_4$, are any 4 amino acids.

In still another preferred embodiment, the subject inositolglycan domain comprises a structure selected from:
EtN-P-[Mα2]Mα2 Mα6 Mα4Gα6Ino
EtN-P-[Mα2][G]Mα2 Mα6 Mα4Gα6Ino
EtN-P-[Mα2][X]Mα2 Mα6 Mα4Gα6Ino
EtN-P-[Mα2][EtN-P]Mα2 Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-Mα2 Mα6 Mα4G
Mα2 Mα6 Mα4G
EtN-P-Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglyean domain comprises a structure selected from:
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 Mα4G
Mα2 [Mα2][X]Mα2 Mα6 Mα4G
Mα2 [Mα2][EtN-P]Mα6 Mα4G
or derivative or equivalent thereof wherein EtN is ethanolamine, P is phosphate, M is mannose, G is non-N-acetylated glucosamine, [G] is any non-N-acetylated hexosamine, Imo is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 Mα6 M
EtN-P-[Mα2][X]Mα2 Mα6 M
EtN-P-[Mα2][EtN-P]Mα2 Mα6 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

In still another preferred embodiment, the subject inositolglycan domain comprises a structure selected from:
EtN-P-[Mα2][G]Mα2 M
EtN-P-[Mα2][X]Mα2 M
EtN-P-[Mα2][EtN-P]Mα2 M
or derivative or equivalent thereof wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substituent, α represents α-linkages which may be substituted with β-linkages wherever required, and numeric values represent positional linkages which may be substituted with any other positional linkages as required.

Still another aspect of the present invention is directed to a pharmaceutical composition comprising a molecule capable of inducing an immune response directed to a micro-organism GPI inositolglycan domain but substantially incapable of inducing an immune response directed to a lipidic domain of a GPI, as broadly described above, together with one or more pharmaceutically acceptable carriers and/or diluents.

The pharmaceutical forms suitable for injectable use include sterile aqueous solutions (where water soluble) and sterile powders for the extemporaneous preparation of sterile injectable solutions or dispersion or may be in the form of a cream or other form suitable for topical application. It must be stable under the conditions of manufacture and storage and must be preserved against the contaminating action of micro-organisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of micro-organisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of expressing, for example, a functional equivalent to a GPI inositolglycan domain or derivative thereof. The vector may, for example, be a viral vector and it may be administered by any suitable method including, for example transfection directly into the cells of the mammal being treated or transfection into a host cell, such as a bacterium, yeast or attenuated parasite, which is then introduced into the mammal.

Administration of the immunogenic GPI inositolglycan domain of the present invention induces antibody production and in particular IgG production, Said antibodies are involved in inhibiting, halting or delaying the onset or progression of symptoms associated with micro-organism infection such as, for example, pathological responses to a parasitic infection. Said antibodies function, for example, by neutralising parasite induced TNF induction or by direct antiparasitic effect such as killing the parasite by binding to its surface and inhibiting its growth or development or otherwise inhibiting its onward progression. Antibodies directed to the GPI inositolglycan domain or derivatives thereof may therefore also be utilised in treating parasitic infections therapeutically or prophylactically.

Accordingly, another aspect of the present invention is directed to antibodies to GPI inositolglycan domains but substantially incapable of interacting with the lipidic domain of a GPI.

Such antibodies may be monoclonal or polyclonal, may be of any isotype and may be selected from naturally occurring antibodies to endogenous or exogenous GPI inositolglycan domains or may be specifically raised to GPI inositolglycan domains. Antibodies may also have been raised against antigens other than the GPI inositolglycan domain but are cross-reactive with one or more epitopes of the GPI inositolglycan domain. In the case of antibodies raised to the GPI inositolglycan domain, a GPI inositolglycan may first need to be associated with a carrier molecule as hereinbefore described.

The antibodies and/or GPI inositolglycan domains of the present invention are particularly useful as therapeutic or diagnostic agents. For example, a GPI inositolglycan domain can be used to screen for naturally occurring antibodies to GPI inositolglycan domain. These may occur, for example in some infectious and autoimmune diseases. Alternatively, specific antibodies can be used to screen for GPI inositolglycan domains. Techniques for such assays are well known in the art and include, for example, sandwich assays, ELISA, Western blot and flow cytometry. Knowledge of GPI inositolglycan domain levels may be important for diagnosis of certain diseases, such as parasitic infections, autoimmune diseases (e.g. Type 1 diabetes), degenerative diseases (erg. Type 2 diabetes) and somatically acquired genetic defects (e.g. Paroxysmal Nocturnal Haemoglobinurea) or for monitoring certain therapeutic protocols. Said antibodies would be useful as research tools or reagents for the detection of GPI inositolglycan domains. Said antibodies would also be important for example as a means for screening for levels of GPI inositolglycan domains in cell extract or other biological fluid or purifying a GPI made by recombinant means from culture supernatant fluids. Techniques for the assays contemplated herein and known in the art and include, for example, sandwich assays and ELISA, Western blot and affinity chromatography.

Antibodies to GPI inositolglycan domain of the present invention may be monoclonal or polyclonal. Alternatively, fragments of antibodies may be used such as Fab fragments. Furthermore, the present invention extends to recombinant and synthetic antibody, to antibody hybrid and to humanised antibody. A "synthetic antibody" is considered herein to include fragments and hybrids of antibodies. The antibodies of this aspect of the present invention are particularly useful for immunotherapy and immunoprophylaxis and may also be used as a diagnostic tool for assessing, for example, parasitic infection or for monitoring the program of therapeutic regimen.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of the GPI inositolglycan domain.

Both polyclonal and monoclonal antibodies are obtainable by immunization with the GPI inositolglycan domain and are utilizable for immunoassays. The methods of obtaining both types of sera are well known in the art. Polyclonal sera are less preferred but are relatively easily prepared by injection of a suitable laboratory animal with an effective amount of a GPI inositolglycan domain, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Yet another aspect of the present invention relates to a pharmaceutical composition comprising an antibody directed to a GPI inositolglycan domain together with one or more pharmaceutically acceptable carriers or diluents as hereinbefore described.

A further aspect of the present invention relates to the use of the antibodies of the present invention in relation to disease conditions. For example, the present invention is particularly useful but in no way limited to use in treating parasitic infections, their symptoms and pathologies.

Accordingly, another aspect of the present invention relates to a method of inhibiting, halting or delaying the onset of progression of a mammalian disease condition characterised by a micro-organism infection said method comprising administering to said mammal an effective amount of an antibody has hereinbefore described.

Preferably said disease condition is a parasite infection and most preferably malaria.

In yet another aspect the present invention relates to the use of an antibody in the manufacture of a medicament for inhibiting, halting or delaying the onset or progression of a disease condition characterised by the infection of a mammal by a microorganism.

Preferably said disease condition is a parasite infection and most preferably malaria.

The present invention is further described by the following non-limiting Examples.

EXAMPLE 1

Reagents, Animals and Preparation of Parasites

Pronase was obtained from Boehringer Mannheim. Phosphatidylinositol-specific phospholipase C was from Calbiochem. Octyl-Sepharose, Protein-G Sepharose, n-octylthioglucopyranoside (n-otg), phenylmethylsulfonylfluoride (PMSF), p-tosyl-L-lysine-chloromethylketone (TLCK), N-tosyl-L-phenylalaninechloromethylketone (TPCK), p-chloro-mercuriphenylsulphonic acid (p-CMPS), aprotinin, leupeptin, pepstatin, iodoacetamide, n-ethyl-maleimide (NEM), and Concanavalin-A were obtained from Sigma Chemical Co. Sephadex was from Pharmacia. Biogel P4 was from Biorad. Analytical or HPLC grade, acetic acid, butanol, chloroform, diethyl ether, ethanol, methanol and water were obtained from BDH and Waters. Silica G60 TLC plates were from Merck Darmstadt. Tritiated mannose, glucosamine, myristic and palmitic acids were from Amersham.

Adult female C57BL/6 and C3H/HeJ mice were bred and maintained in the Walter and Eliza Hall Institute specific pathogen free animal facility.

The FCB-1 line of *Plasmodium falciparum* were grown in vitro by standard methods, and confirmed free of *Mycoplasma* contamination. For the biosynthetic labelling of parasite proteins, 3H-palmitic acid conjugated to defatted bovine serum albumin in molar ratio 1:1, 3H-glucosamine or 3H-mannose were added at a final specific activity of 10 µCurie/ml, to RPMI 1640 cultures of $2 \times 10^{10}$ parasites at the late trophozoite/early schizont stage for 2 hours (for labelling of GPI precursors) or 8 hours (for labelling of protein-bound GPI). Parasites were harvested by 0.05% Saponin lysis and centrifugation in the cold at 15,000 g for 20 minutes, followed by two washes in PBS and storage at –70C.

EXAMPLE 2

Purification of the 195KD MSP-1 and 56KD MSP-2 Antigens

The GPI-anchored MSP-1 and MSP-2 merozoite surface proteins were purified to homogeneity as described previously (Schofield and Hackett, 1993), Biosynthetically labelled malaria parasites at the late schizont stage were lysed in 0.05% Saponin and centrifuged at 15,000 g for 20 minutes, and washed as above. The pellet was extracted in 25 mM n-octyl-thioglucopyranoside (n-otg), 1% BSA, 1 mM EDTA, 0.1 mM EGTA, 1 mM PMSF, 1 mM TPCK, 0.1 mM TLCK, 5 mM pCMPS, 1 µg/ml pepstatin, 1 µg/ml leupeptin, 1 mM NEM, 5 mM iodoacetamide, 150 mM NaCl, 25 mM Tris/HCl pH 7.4 by sonication on ice. The extact was clarified by centrifugation at 20,000 g for 30 minutes in the cold, and the supernatant decanted and loaded onto two immunoaffinity columns arranged in sequence, containing approximately 10 mg monoclonal antibody 111.4 or monoclonal antibody 113.1, each cross-linked to Protein G-Sepharose by gluteraldehyde (all procedures on ice). The protein extract was passed through the column at a rate of 0.3 ml/min. The columns were washed first with 100 ml 10 mM n-otg, 1% BSA, 300 mM NaCl, followed by 100 ml 10 mM n-otg, 300 mM NaCl. Antigen was eluted from each column with four column volumes of 10 mM n-otg, 200 mM glycine pH 2.8. The pH of the eluate was neutralized with 2M Tris. Aliquots of protein were analysed for purity by SDS-PAGE followed by staining with Coomassie brilliant blue. The remaining purified proteins were dialysed exhaustively against 100 mM $NH_4HCO_3$ using dialysis membrane previously boiled exhaustively in 10 mM EDTA followed by boiling in 10 changes of double distilled water. Protein concentration was determined by standard methods.

The remaining detergent soluble extract was made up to 1 mM $CaCl_2$, 1 mM $MgCl_2$, and 1 mM $MnCl_2$, and passed over a Con-A sepharose column, followed by washing with 10 column volumes of extraction buffer. The column was first eluted with detergent buffer containing 0.5M α-methyl-mannopyranoside and 0.5M α-glucopyranoside, followed by 25 mM n-otg in 8M urea. Aliquots were subject to SDS-PAGE and fluorography or staining with Coomassie blue.

EXAMPLE 3

Purification of the C-Terminal GPI Anchors of Defined Parasite Antigens

To purify the intact C-terminal GPIs free of detergent, non-covalently bound lipids, glycolipids, phospholipids and protein or peptide fragments, affinity purified MSP-1 and MSP-2 were first scrubbed with organic solvents. 10 mg/ml GPI-anchored proteins were placed in 150 µl aliquots in clean glass tubes. 600 µl MeOH was added and vortexed, followed by 150 µl 1 Chloroform and 450 µl water and further vortexing. The samples were centrifuged at 14000 rpm for 3 min, the supernatant discarded, and the interphase and lower phase mixed with 450 µl MeOH and re-centrifuged at 14000 rpm for 3 min. The protein pellet was extracted 5 times with C/M/W 10:10:3, and finally extracted with acetone over night at −20 C. The acetone was removed completely and the proteins taken up with sonication in 6M Urea, 1 mM DTT, 1 mM iodoacetic acid. After 15 minutes at room temperature, the sample was diluted 6 fold and made to 5 mM $CaCl_2$. 2.5% pre-digested Pronase B was added for 72 h at 37 C with 2 additions of 0.3% pronase. The digested sample was phase separated between water and water-saturated butanol, and the organic phase back extracted with water. The butanol phase was spotted onto TLC plates (Si-60) and run in the solvent system C/M/HAc/W 25:15:4:2. The pronase-digested GPI fragment free of contaminants remains close to the origin, and was detected by Berthold Digital Autoradiograph. The appropriate region was scraped and the material eluted twice with C/M/W 10:10:3 followed by 40% 1-propanol in water. The material was dried under nitrogen gas, and once more separated between water and water-saturated butanol.

EXAMPLE 4

Purification of GIPLs and GPI Biosynthetic Precursors by TLC

GPI biosynthetic intermediates and non-protein bound mature GPI species were purified by TLC. $2\times10^{10}$ *P. falciparum* schizonts were labelled with 1 mCi $^3$[H]-nannose or $^3$[H]-palmitic acid in 250 ml glucose deficient RPMI 1640 supplemented with 40 mM fructose and 0.5% Albumnax (GIBCO) for 2 hours. Parasites were harvested by saponin lysis and washed twice in PBS. They were extracted three times in chloroform methanol (2:1) and three times in chloroform/methanol/water (1:1:0.3). The chloroform/methanol extracts were subject to repeated Folch washing and the chloroform phase dried in a Speedvac. The chloroform/methanol/ water extracts were dried down and partitioned between water and water-saturated butanol. The butanol phase was washed with water and dried in a Speedvac. Both residues were then separated by TLC and the plates scanned by Bertold Digital Autoradiograph TLC scanner. The radiolabelled peaks were identified and removed by scraping and re-extraction followed by drying. Areas lying between and outside the identifiable peaks were treated in the same way, as were sham plates. In some experiments, the GPIs were further purified over Octyl-Sepharose. Samples were taken up in 5% 1-propanol in 100 mM Ammonium acetate and loaded at a flow rate of 0.1 ml/min onto an Octyl-Sepharose column, and the column washed with 100 mM Ammonium acetate, 5% 1-propanol. The column was eluted in a gradient running from 100 mM Ammonium acetate, 5% 1-propanol to 60% 1-propanol in water. GPI containing fractions were lyophilised and flash evaporated in methanol.

EXAMPLE 5

Generation of Chemical and Enzymatic Hydrolysis Fragments of GPIs

Purified, glucosamine-labelled *P. falciparum* GPIs, in which all dpms were detected in the organic phase following butanol/water partitioning, were subject to base hydrolysis by suspension in methanol/ammonia 1:1 for 6 hours at 50 C, followed by partioning between water and water saturated butanol. Essentially 100% of label was then recovered from the aqueous phase. The aqueous phase was twice extracted with water-saturated butanol, lyophilized, and flash evaporated with methanol.

EXAMPLE 6

DEAE Anion Exchange Chromatography

GPIs were loaded onto a A DEAF column in 99% methanol, 1% water and washed with ten column volumes of solvent. They were subsequently eluted in 100 mM Ammonium Acetate in 99% methanol, 1% water and dried under Nitrogen.

EXAMPLE 7

Biogel P4 Size-Exclusion Chromatography

Base-hydrolyzed GPI glycols were spiked with phenol red and blue dextran in 100 mM Ammonium Acetate and further size-fractionated by passage through a 1 cm×1.2 meter Biogel P4 column equilibrated in 100 mM Ammonium acetate in water. The column had previously been exhaustively calibrated by repeated analytical runs with GPI mixed with acid hydrolyzed dextran markers to yield the relative elution position of glucose units detected by staining with ordinal in concentrated sulfuric acid. The column runs proved to be highly reproducible. For preparative purposes the dextran markers were omitted. The GPI peak was detected by scintillation counting of aliquots.

EXAMPLE 8

Compositional Analysis by GC/MS

Glycan concentration and compositional purity was determined by GC-MS, following acid methanol sis and trimethylsilyl (TMS) dramatization. myo-Inositol content was measured following acid hydrolysis (6N Hal, 110° C., 16 h) and TMS dramatization, with selected ion monitoring for m/z 305 and 318. Scylla-Inositol was used as internal standard throughout.

EXAMPLE 9

Coupling of GPI Glycan to Maleimide-Activated KLH

The GPI glycan was exposed to 1mM Traut's reagent (2-iminothiolane) in 60 mM triethaniolamine, 7 mM potassium phosphate, 100 mM NaCl, 1 mM EDTA, pH 8.0 in the cold for 90 minutes under nitrogen. The sample was then desalted by gel filtration at 4 C through a small Biogel P4 column equilibrated in 7 mM potassium phosphate, 100 mM NaCl, 1 mM EDTA, pH 7.2 and added to maleimide-activated KeyHole Limpet Haemocyanin (KLH) or Ovalbumin (OVA) in coupling buffer (7 mM potassium phosphate, 100 mM NaCl, 1 mM EDTA, pH 7.2) overnight. The degree of conjugation was estimated by comparison of cpms before and after dialysis of the sample against PBS, or by use of Ellman's reagent for the quantitation of sulfhydryl groups. Excess reactive sites were blocked with cysteine.

EXAMPLE 10

Epitope Mapping of Anti-GPI Antibodies

Coupling of the purified GPI glycan to proteins was undertaken as above. To measure anti-lipid reactivities, we utilized commercially available phosphatidylinositol from Sigma with identical composition to the malarial GPI, namely dipalmitoyl-PI. 2 mg PI was coupled to defatted BSA according to published protocols (Bate et al, 1993).

EXAMPLE 11

ELISA Assay

Antigen (GPI-OVA, Glycan-OVA, BSA-PI, OVA or BSA alone) at 20 μg/ml in phosphate binding buffer was incubated overnight in 50 μl volumes in flat-bottomed Immunlon 96-well plates, followed by extensive washing with buffer. The plates were blocked with 1% BSA, 1% OVA in PBS for several hours. From a 1/32 dilution, sera were titrated two-fold in 1% BSA, 1% OVA in PBS, and 50 μl aliquots incubated in triplicate for 2 hours at room temperature, followed by extensive washing with 1% BSA, 1% OVA 0.05% Tween-20 in PBS. An aliquot of affinity purified, biotin-labelled isotype specific goat anti-mouse second antibody was incubated as above, followed by further washing and the addition of streptavidinh-alkaline phosphatase. After 30 minutes the plates were washed again and colourimetric development initiated by the addition of p-Nitrophenylphosphate in diethanolamine buffer. Background binding to BSA/OVA-coated plates was determined in parallel. The end-titres derived are the last point giving values statistically different by two-way analysis of variance from non-specific binding by the same serum to the BSA/OVA-coated plates.

EXAMPLE 12

Competition ELISA

From a 1/32 dilution, sera or mAbs were titrated two-fold in 1% BSA in PBS, 0.05% Tween-20, and pre-incubated for 4 hours at room temperature with a molar excess of competitor (20 μg/ml PI, or phosphatidylserine (PS), or diluent alone). Antigen (BSA-PI or BSA alone) at 20 μg/ml in phosphate binding buffer was incubated overnight in 50 μl volumes in flat-bottomed Immunlon 96-well plates, followed by extensive washing with buffer. The plates were blocked with 1% BSA in PBS for several hours. 50 μl aliquots of titrated antibody with or without competitor were incubated in triplicate for 2 hours at room temperature, followed by extensive washing with 1% BSA 0.05% Tween-20 in PBS. An aliquot of affinity purified, biotin-labelled isotype specific goat anti-mouse second antibody was incubated as above, followed by further washing and the addition of streptavidinh-alkaline phosphatase. After 30 minutes the plates were washed again and colourimetric development initiated by the addition of p-Nitrophenylphosphate in diethanolamine buffer. Background binding to BSA-coated plates was determined in parallel. The end-titres derived are the last point giving values statistically different by two-way analysis of variance from non-specific binding by the same serum to the BSA-coated plates.

EXAMPLE 13

Production of Monoclonal Antibodies

Monoclonal antibodies to the lipid domain of the GPI were produced as previously described (Tachado et al, 1996). Monoclonal antibodies to the glycan were generated by immunization of OVA-TCR transgenic mice on a Balb/c background with OVA-glycan, followed by fusion and screening of hybridoma culture supernatants against BSA vs. BSA-glycan.

EXAMPLE 14

Macrophage Culture and TNF Output

LPS-nonresponsive C3H/HeJ macrophages were obtained as previously described (Schofield and Hackett, 1993 and Tachado et al, 1996). $2 \times 10^5$ adherent cells/well were given medium alone or test agents. 3 hrs after incubation TNF-α levels in the supernatant and standard curve were determined by capture ELISA (Pharmingen).
Tyrosine Phosphorylation.

Rapid onset tyrosylphosphorylation was determined as previously described (Tachado et al, 1997).

EXAMPLE 15

PI-PLC Treatment and FACS Analysis $2 \times 10^5$ cells were exposed to 1 U/ml PI-PLC at 37 C for 2 hours, followed by washing. They were then incubated in ice cold murine tonicity RPMI 1640 with 0.05% Sodium azide and 1% BSA with monoclonal antibodies or murine sera followed by washing and a further incubation with isotype-specific FITC-conjugated antibody to mouse immunoglobulins. After washing in the same medium the cells were counter-stained with 0.5 μg/ml propidium iodide and analysed by FACSscan.

EXAMPLE 16

Immunization of Mice with Free GPI

Figure 2:
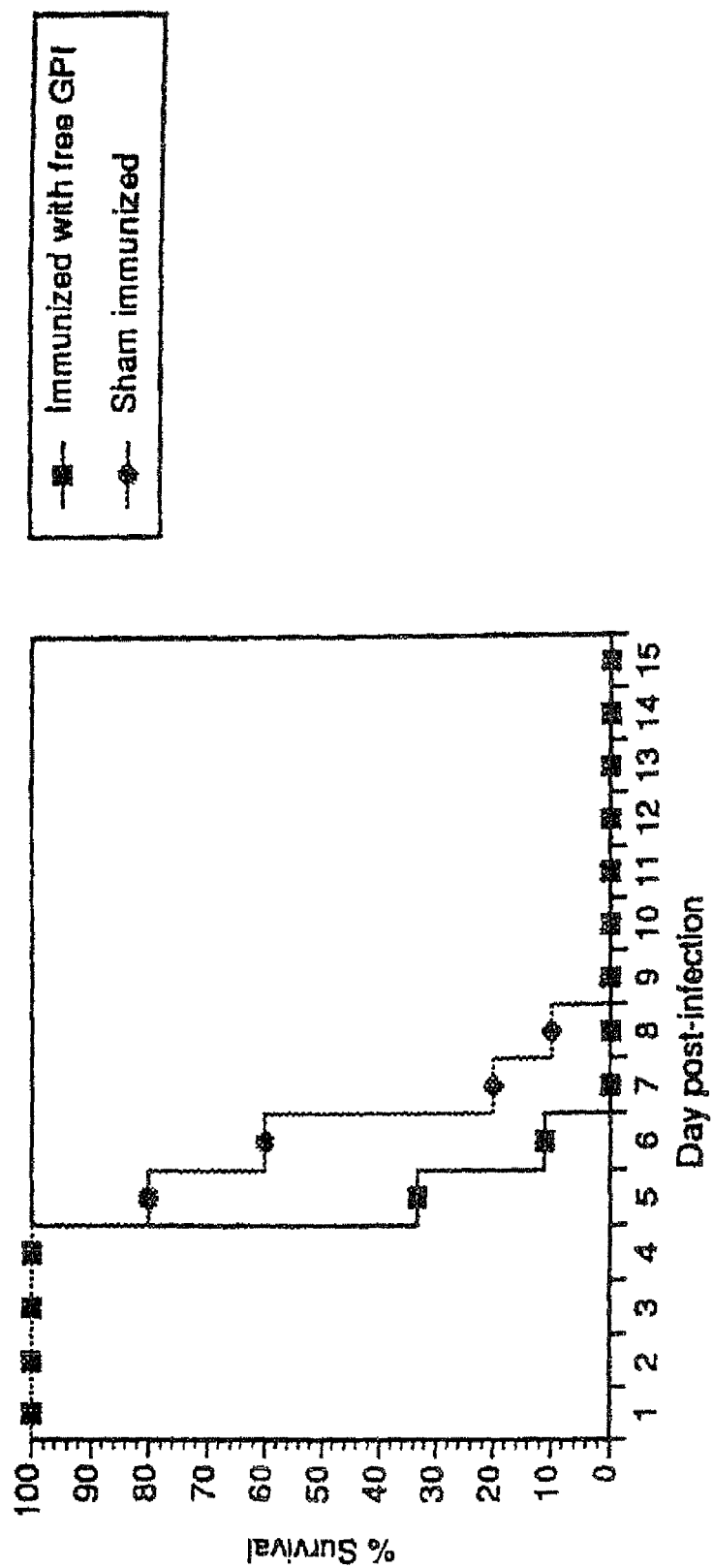
FIG. 2 is a graphical representation of the results of C57B1/6 mice immunized with free GPI in IFA and sham-immunized mice (IFA alone) which were challenged with *P. berghei* ANKA and survival assessed over 15 days.

Mice were immunized by three successive boosts of free intact malarial GPI emulsified in Incomplete Freund's Adjuvant spaced two weeks apart. Control mice received an equal amount of IFA alone. After immunization, sera were bled and the titres of anti-GPI antibodies determined by ELISA. All animals immunized with GPI developed broadly similar levels of anti-GPI antibodies (range 1/1024-1/4096) among individual animals. The anti-GPI response was predominantly IgM, and epitope mapping studies by competition ELISA revealed that the antibody response was directed predominantly towards the lipidic (phosphatidylinositol, PI) domain of the molecule, with some cross-reactivity to other phospholipid determinants (FIG. 1). Two weeks after the final boost mice were challenged with *P. berghei* ANKA. Parasitaemia, the development of neurological complications, and mortality were recorded daily. No difference in parasitaemia was observed. In the control group, 100% of animal manifested between day 5 and 9 an aggressive cerebral syndrome with neurological signs proceeding to rapid death with 12 hours. In animals immunized with intact free GPI, however, deaths occurred at a noticable faster rate (FIG. 2).

Figure 3:
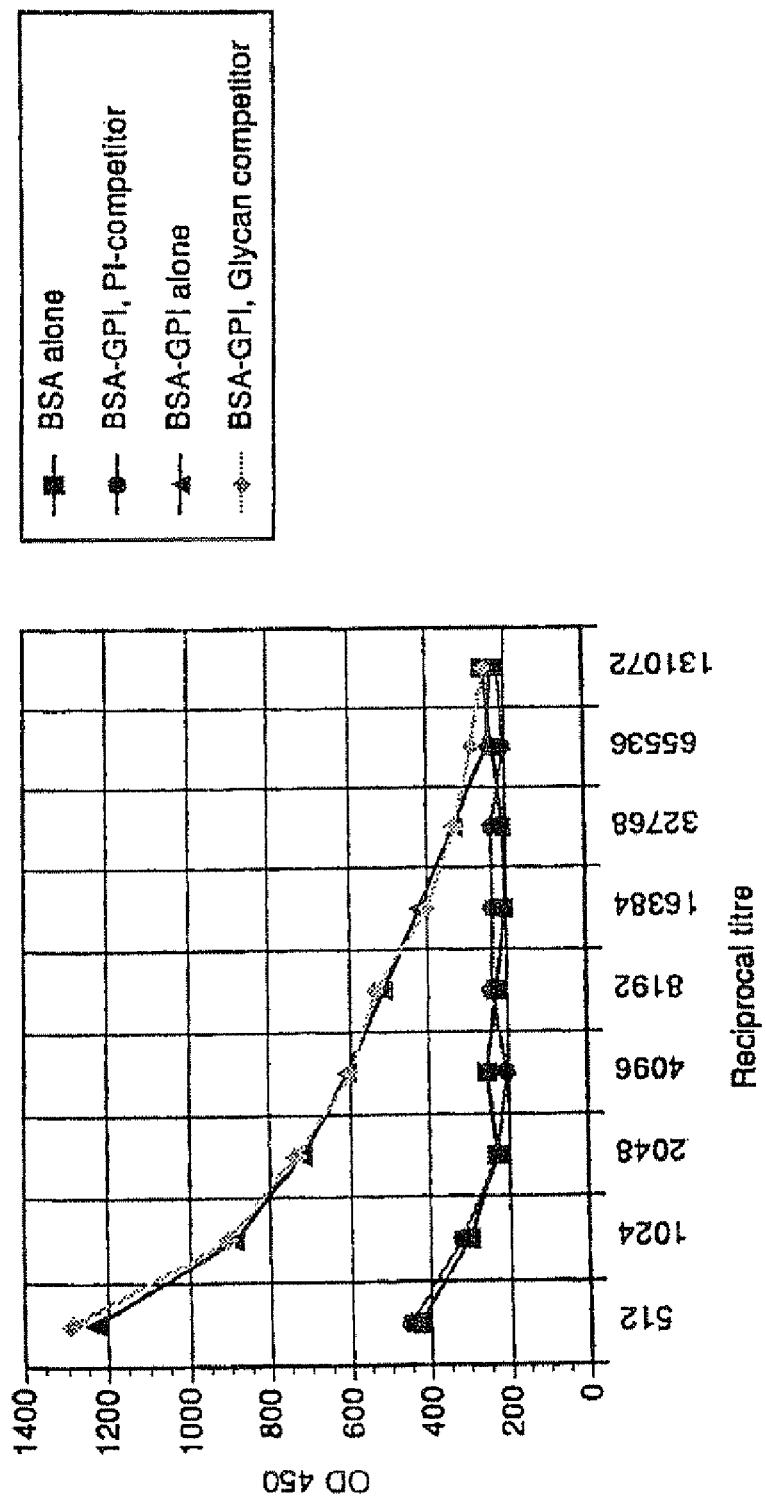
FIG. 3 is a graphical representation of the epitope mapping of anti-lipid monoclonal antibodies. Monoclonal antibody 1C7 to GPI derived from mice immunized with free GPI (1,5) were screened by competition ELISA for reactivity with GPI in the presence or absence of PI and GPI glycan competitors.
Figure 4:
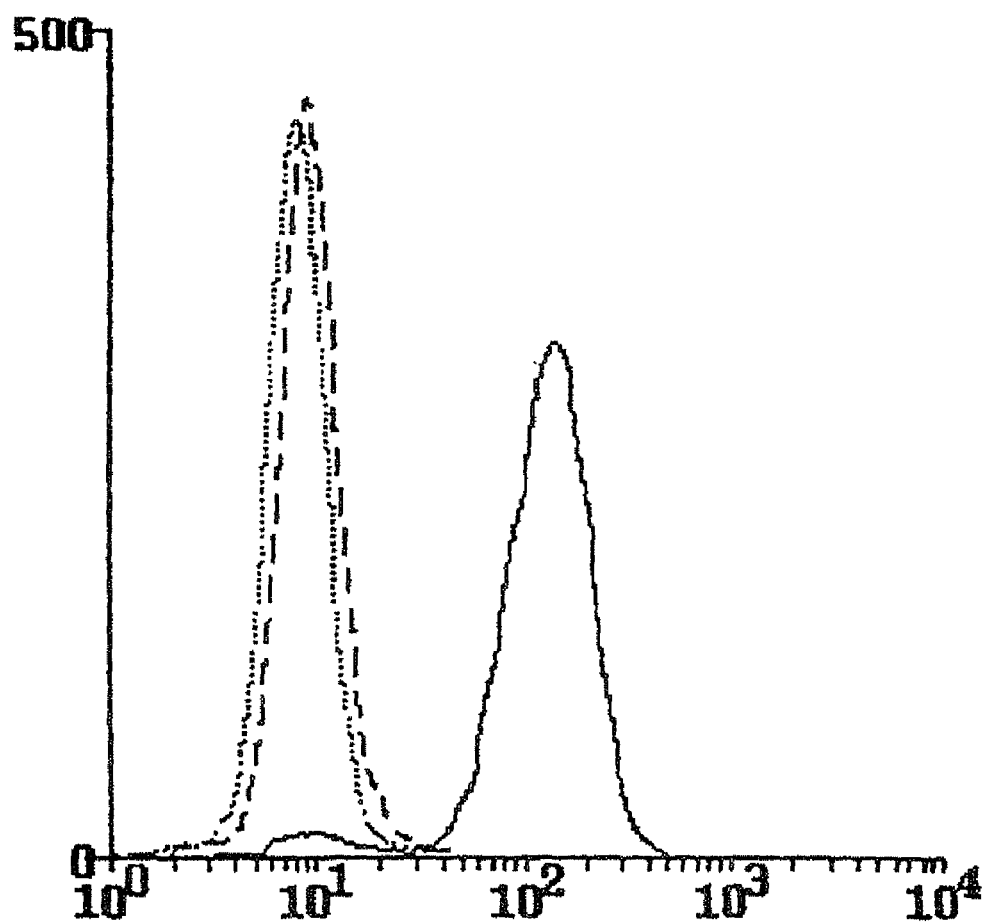
FIG. 4 is a graphical representation of monoclonal antibody 1C7, to malarial GPI lipid domains, recognition of mammalian GPIs at the cell surface as determined by FACS analysis. Solid line, binding of 1C7 to macrophages; dotted line, no antibody; dashed line, binding of 1C7 following PI-PLC treatment of macrophages.
Figure 5:
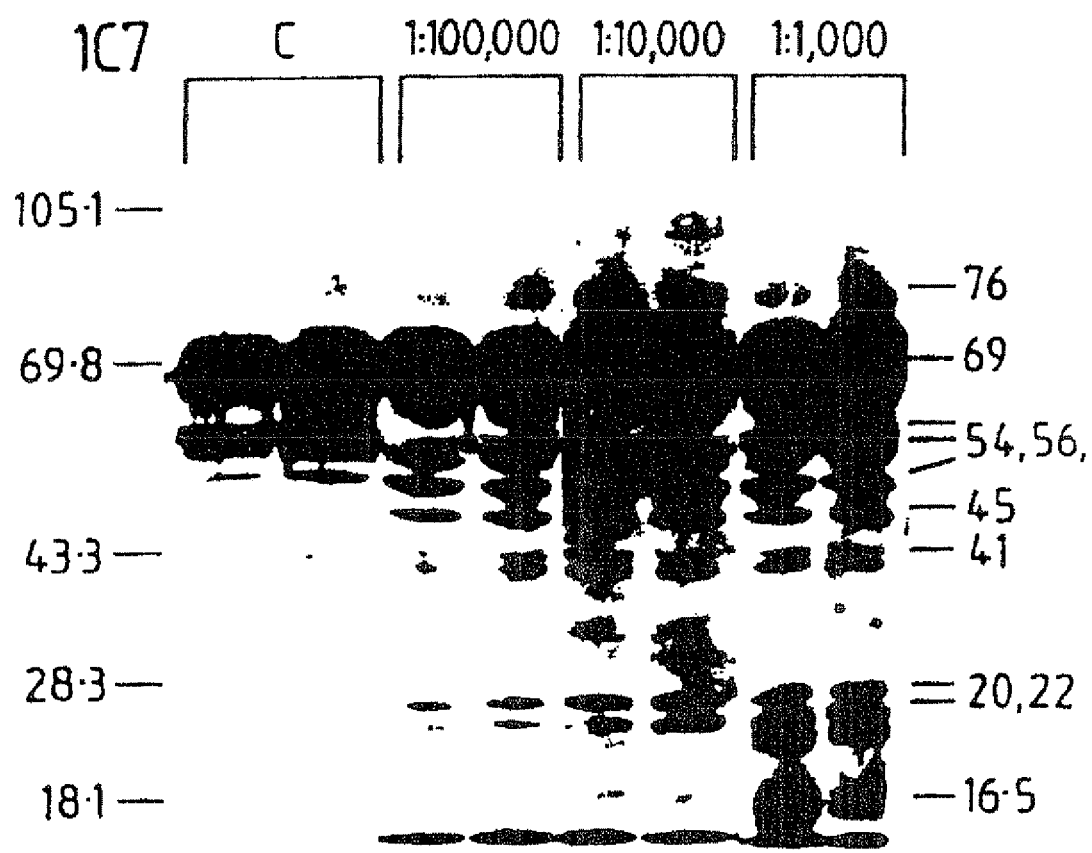
FIG. 5 is a photographic representation of monoclonal 1C7, to lipid domain of the GPI, induction of rapid onset tyrosylphosphorylation in host cells.
Figure 6:
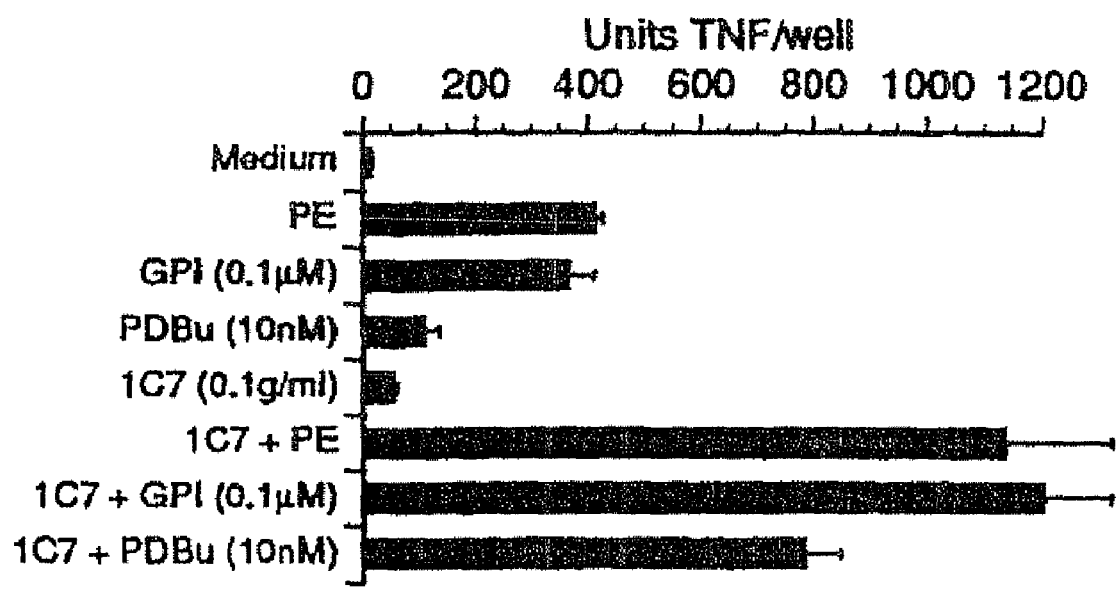
FIG. 6 is a graphical representation of monoclonal 1C7 synergizy with GPI, phorbol esters and parasite extracts in the induction of TNF output from murine C3H/HeJ macrophages.
Figure 7:
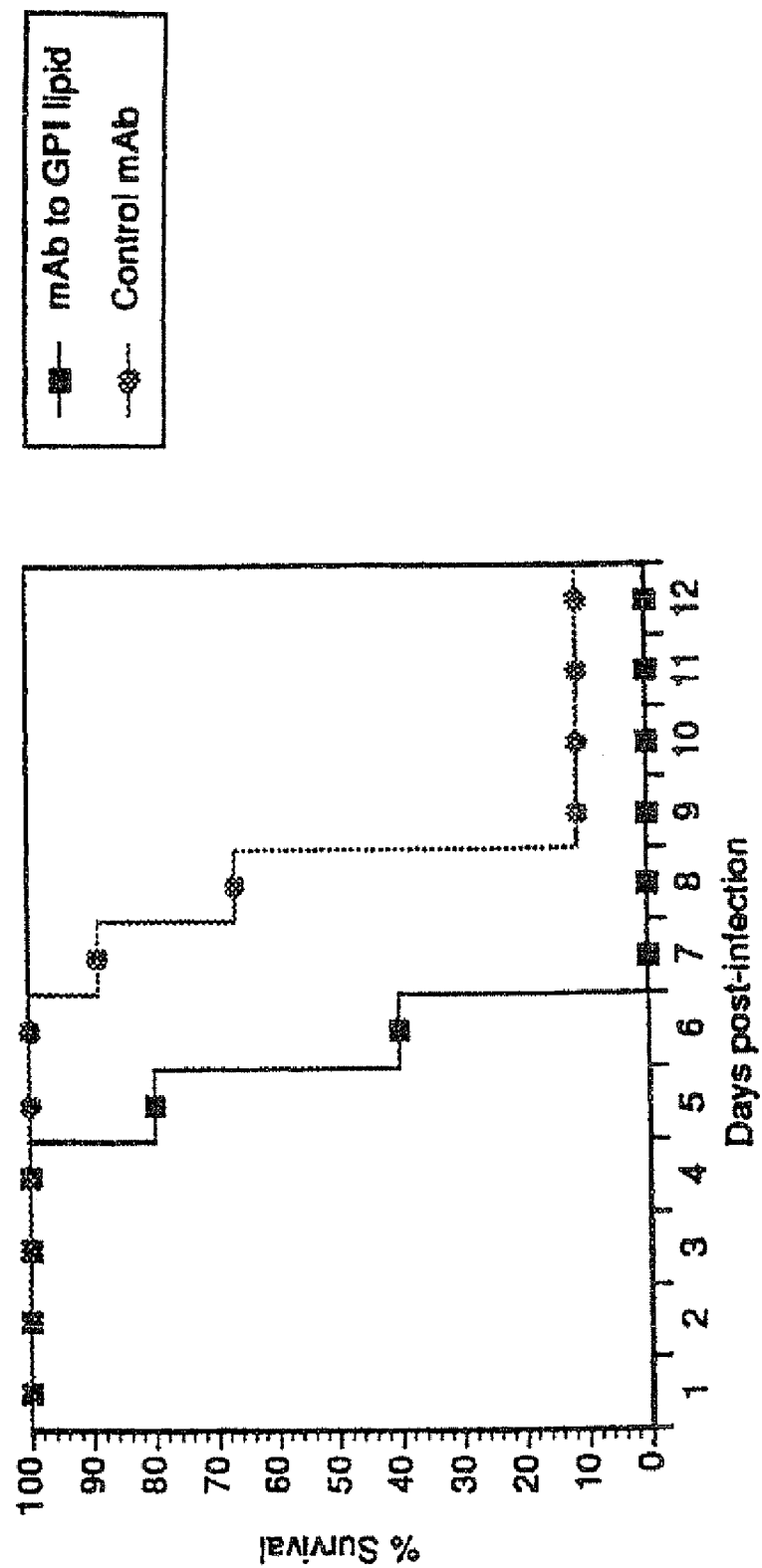
FIG. 7 is a graphical representation of monoclonal 1C7 exacerbation of the *P. berghei* ANKA cerebral malaria syndrome in C57B1/6 mice.

The increased death rate in animals immunized with free GPI and subsequently challenged with malaria may result from unanticipated autoreactivity of anti-GPI antibodies. A panel of IgM monoclonal antibodies was derived from mice immunized with free GPIs. mAbs selected at random from this panel were shown by PI-specific ELISA to be reactive with PI domain of the molecule (FIG. 3), as was expected given the established serological specificity of the polyclonal sera of the donor immunized mice (FIG. 1). In addition, these mAbs and the polyclonal antisera of GPI-immunized mice were shown by FACS analysis to react with host GPI molecules expressed at the cell surface. Although surprising, the recognition of GPI-associated lipidic determinants at the cells surface is not without precedence (Xia et al., 1993). Pre-treatment of host cells with phosphatidylinositol-specific phospholipase C resulted in loss of binding of these mAbs, demonstrating formally that a lipidic moiety of GPI molecules is exposed at the cell surface and is accessible for binding by autoreactive antibodies generated in response to exposure to free malarial GPI (FIG. 4). The binding was also shown to cause massive rapid onset intracellular tyrosine phosphorylation (FIG. 5), a well-known and predictable consequence of cross-linking host GPIs at the cell surface (Shenoy-Scaria et al, 1992 and Stefanova et al 1993). Following binding of these antibodies to macrophages, the cells responded more vigorously to stimulation with GPI, phorbol esters or malaria parasite extracts (FIG. 6). Upon passive transfer into mice, these mAbs were sufficient to cause an increased rate of death as compared with control IgM mAbs (FIG. 7).

Thus to summarize: (i) immunization of mice with the free *P. falciparum* GPI generates IgM reacting predominantly with the PI domain of the GPI; (ii) this immunization appears to exacerbate the *P. berghei* cerebral malaria syndrome; (iii) exacerbated pathogenicity as detected by increased death rate was also observed upon passive transfer of IgM monoclonals with the same reactivity; (iv) the mAbs were shown to cross-react with host GPIs by FACS analysis, thereby causing massive intracellular tyrosylphosphorylation and sensitization of macrophages resulting in increased TNF output in response to addition agonists. Therefore it is proposed that a novel mechanism exists by which the acquisition of certain autoreactive immunological specificities results in increased physiological sensitization to malarial toxins.

EXAMPLE 17

Immunization of Mice with the GPI Glycan Conjugated to KLH

Figure 8:
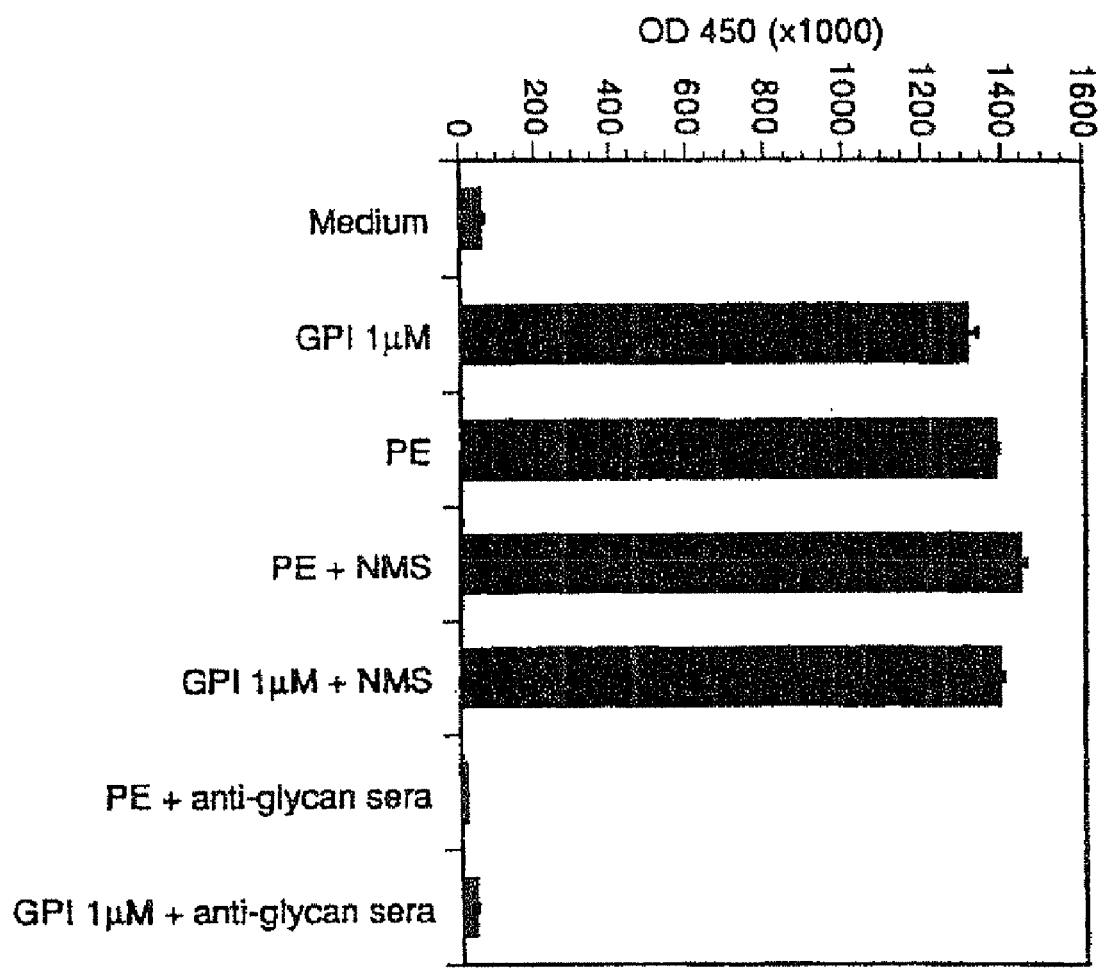
FIG. 8 is a graphical representation of polyclonal antisera from mice immunized with the purified *P. falciparum* GPI glycan covalently conjugated to a protein carrier inhibiting TNF output from macrophages in response to GPI or total parasite extracts. Values show absorbance at 450 mM by anti-TNF ELISA (Pharmingen) and are proportional to mass TNF.

Previous publications dealing with the prospect of anti-disease vaccines against malaria have proposed immunizing against a phospholipid domain within the putative toxin (Bate et al, 1992c, Bate et al, 1992a, Bate et al, 1992b, Bate et al, 1993, Jakobsen et al, 1993b, Bate and Kwiatkowski, 1994 and Playfair, 1994). The present data indicate strongly that this may be deleterious and should be avoided. It was sought to develop a novel approach, namely to detoxify and deacylate the GPI and to determine whether immunization against the glycan domain of the molecule would exacerbate disease or be sufficient to protect mice against malarial pathology. Mice (n=7) were immunized by three successive boosts of 50 µg KLH-glycan emulsified in Incomplete Freund's Adjuvant spaced two weeks apart. Two separate control groups (n=8 each) comprised animals receiving an equal amount of sham conjugated KLH in IFA, or those left untreated. After immunization, sera were bled and the titres of anti-GPI antibodies determined by ELISA. All animals immunized with KLH-glycan developed detectable anti-GPI glycan IgG antibodies, although there were differences in end-titre (range 1/128-1/4096) among individual animals. The sera from vaccine recipients (but not sham-KLH controls) were able to inhibit TNF output from macrophages stimulated with crude *P. falciparum* extracts, providing convincing proof-of-principle for the neutralization of pathogenicity (FIG. 8). In contrast to the host-reactive antibodies to the GPI lipid domain, pre-exposure of macrophages to these sera did not result in increased TNF output in response to additional agonists. With these sera it was not possible to detect significant cross-reactivity with host GPIs at the cell surface as judged by FACS analysis of antibody binding to host cells.

Figure 9:
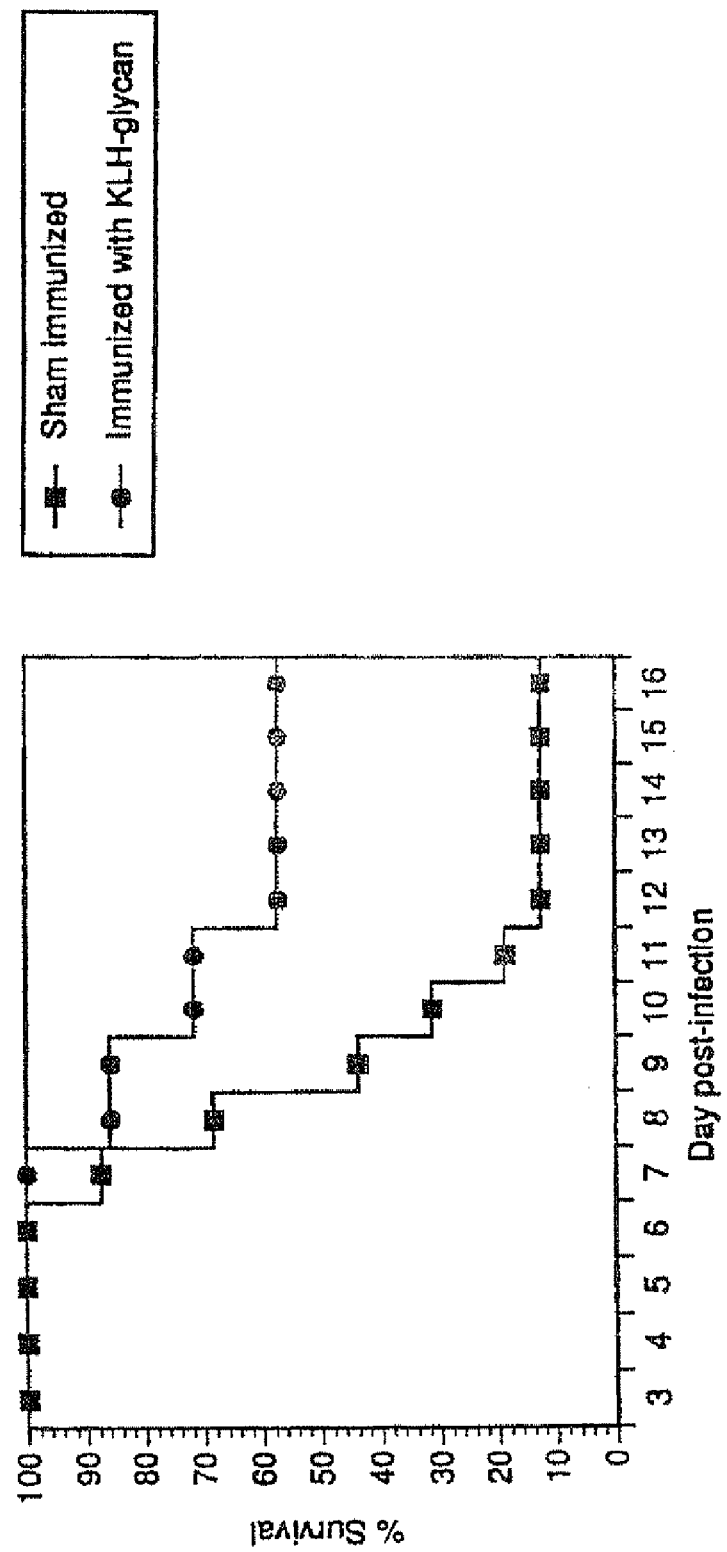
FIG. 9 is a graphical representation of immunization of C57B1/6 mice with the purified *P. falciparum* GPI glycan covalently coupled to KLH providing a significant level of protection against the cerebral malaria syndrome induced by *P. berghei* ANKA.

The *P. berghei* ANKA murine cerebral malaria model has many features in common with the human cerebral malaria syndrome. It is a TNF-α and interferon-γ(IFN-γ) dependent encephalitis associated with upregulation of ICAM-1 on the cerebral microvascular endothelium, an increase in both parasite and macrophage/neutrophil adherence to these target cells, and attendant neurological complications. Unlike human cerebral malaria, there is a breakdown of the blood-brain barrier in the terminal stages of the murine syndrome. However, in the proximal stages the murine disease reflects more accurately the inflammatory cascade leading to cerebral involvement in humans. To determine whether anti-GPI immunization prevents cerebral pathogenesis in vivo, mice were immunized with *P. falciparum* IPG conjugated to KLH. Two weeks after the final boost mice were challenged with *P. berghei* ANKA. Parasitaemia, the development of neurological complications, and mortality were recorded daily. No difference in parasitaemia was observed among groups. In both control groups, 87.5% of animal manifested between day 7 and 12 an aggressive cerebral syndrome with neurological signs proceeding to rapid death with 12 hours, and 12.5% did not develop the syndrome. As there were no significant differences between sham-immunized and untreated groups, the data from these two control groups are pooled (FIG. 9). In recipients of KLH-glycan, one animal (14.2%) died with similar kinetics, two animals (28.5%) developed the cerebral syndrome with substantially delayed kinetics (on days 10 and 11, and showing prolonged course of syndrome before succumbing), and four animals (57.2%) were completely protected, failing to develop the cerebral syndrome at any stage (FIG. 9). Thus immunization of mice with the *P. falciparum* GPI glycan covalently linked to a carrier protein affords substantial protection against the *P. berghei* cerebral malaria syndrome.

Figure 10:
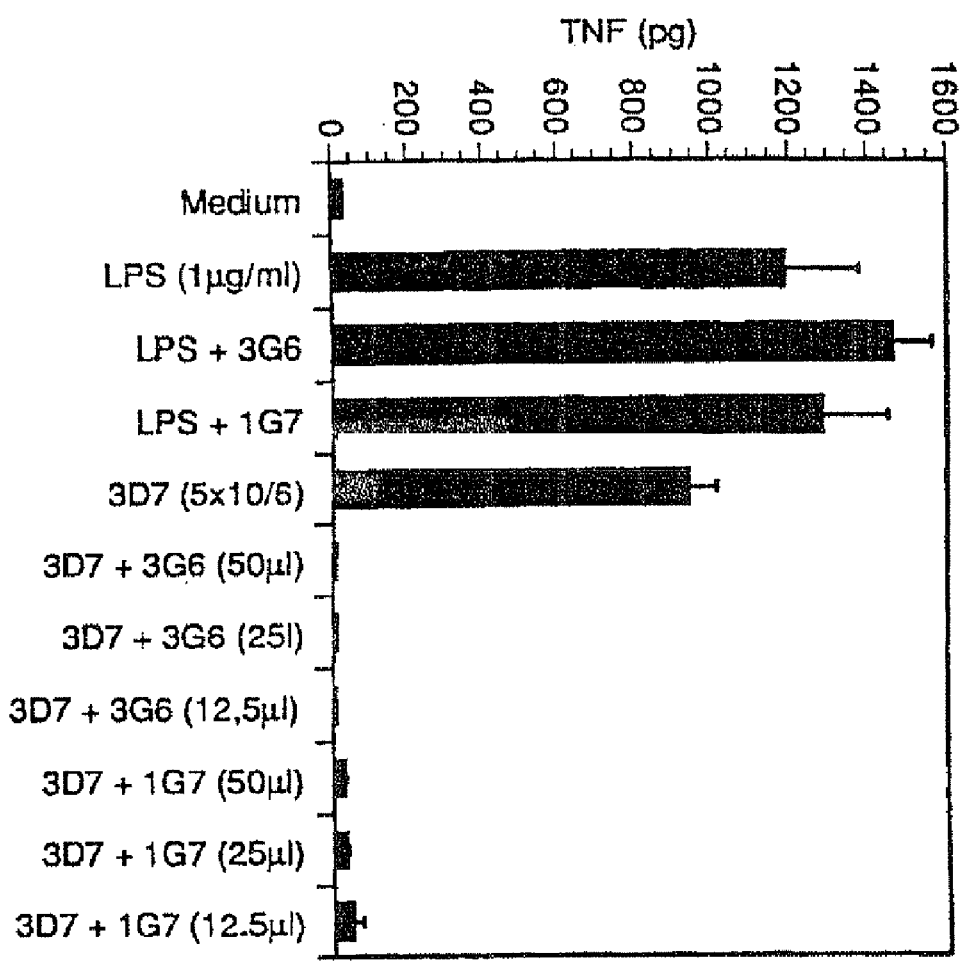
FIG. 10 is a graphical representation of GPI being the dominant TNF-inducing toxin of *P. falciparum*. Monoclonal antibodies 1G7 and 3G6 specific for the GPI glycan derived from OVA-TCR mice immunized with OVA-glycan inhibiting TNF output from macrophages in response to total parasite extracts.
Figure 11:
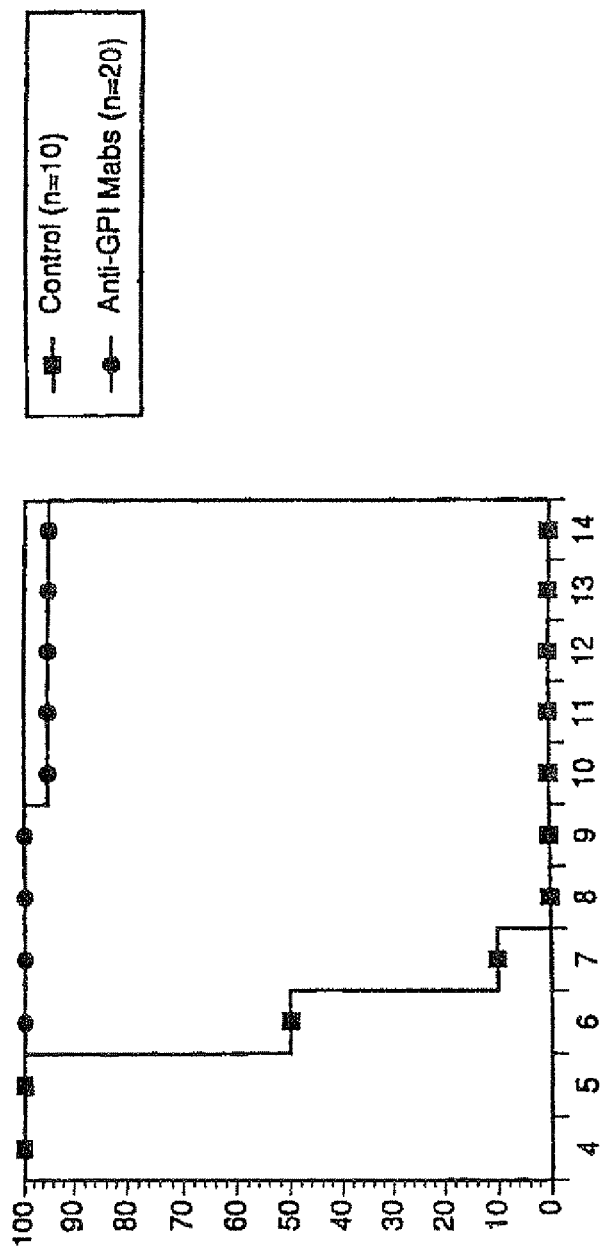
FIG. 11 is a graphical representation of monoclonal antibodies to the *P. falciparum* GPI inositolglycan, upon passive transfer, substantially protecting mice against cerebral malaria and other pathologies.

A panel of monoclonal antibodies was made from mice immunized with purified GPI glycan conjugated to OVA (OVA-glycan). The hybridoma fusion products were initially screened for binding to BSA-glycan as compared to BSA alone. Over 80 glycan-reactive IgG monoclonal antibodies were detected. Of these, many were reactive with parasites but not host erythrocytes as judged by the Indirect Fluorescent Antibody Test. Purified monoclonal antibodies 1G7 and 3G6 were sufficient to block the induction of TNF by 100% when added at low concentration to total crude parasite extracts (FIG. 10). To determine whether anti-GPI antibodies alone are sufficient to prevent severe malarial pathology, mice were infected with $10^6$ P. berghei ANKA i.p. On day 4 they were divided at random into 10 controls receiving an irrelevant IgG and groups of 5 receiving mAbs 1D12, 2C4, 3G5 and 4C3 raised against the P. falciparum GPI inositolphosphoglycan. All mice received 100 μg antibody/day i.p. for 7 days. Mice were monitored for parasitaemia daily and clinical signs every 6 hours. 100% of controls died of the cerebral malaria syndrome between days 6 and 8 post-infection. Throughout this period, no animals receiving either of the 4 anti-GPI monoclonal antibodies showed signs of illness, despite being equally parasitized as controls. On day 10 one of the 5 animals receiving monoclonal 3G5 died. Other than this individual, no others showed cerebral signs and none died (FIG. 11). Thus 19/20 (95%) of the 20 animals receiving anti-GPI mAbs survived, vs. zero survival in controls (n=30 total). Parasitaemias were identical in test and control groups throughout the experiment. For visual clarity, the figure shows the 4 treatment groups in aggregate. In addition, 5 mice received antibodies alone without parasite challenge. There were no detectable acute or toxic reactions in these mice receiving antibodies alone.

Figure 12:
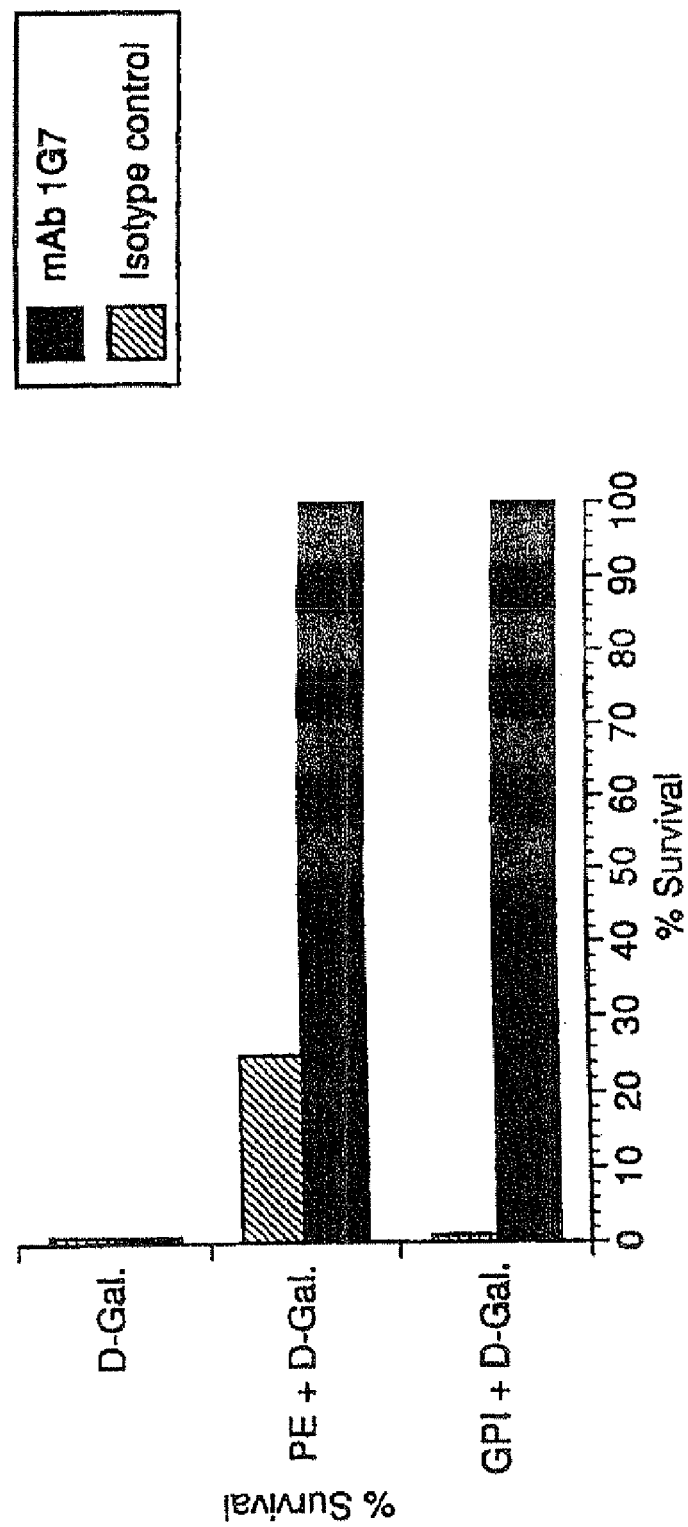
FIG. 12 is a graphical representation of monoclonal antibodies to the *P. falciparum* inositolglycan, upon passive transfer, protecting mice against parasite-induced lethal toxic shock.

In addition a standard murine model of TNF-driven lethality Was used to determine whether GPI mediates parasite-induced acute toxic shock. This model manifests disseminated intravascular coagulation, peripheral vascular failure and shock, and thus has clinical features in common with the human "algid malaria" syndrome. LPS-non-responsive C3H/HeJ and C57B16 mice were primed with 20 mg D-galactosamine followed after 1 hour by purified GPI, PE or PBS alone. Mice receiving), D-galactosamine followed by vehicle alone showed 100% survival. Both PE and purified GPI induced lethal shock in 100% of D-galactosamine-primed C3H/HeJ and C57B16 recipients. mAbs to the GPI glycan substantially prevented TNF-driven lethality in vivo (FIG. 12).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more said steps or features.

BIBLIOGRAPHY

Bate, C. A. W., and Kwiatkowski, D. (1994) *Infection and Immunity* 62:5261-5266.

Bate, C. A. W., Taverne, J., and Playfair, J. H. L. (1992c) *Infection and Immunity* 60:1894-1901.

Bate, C. A., Taverne, J., and Playfair, J. H. (1989) *Immunology* 66:600.

Bate, C. A., Taverne, J., and Playfair, J. H. (1988) *Immunology* 64:227.

Bate, C. A., Taverne, J., Román, E., Moreno, C., and Playfair, J. H. L. (1992a) *Immunology* 75:129-135.

Bate, C. A. W., Taverne, J., Kwiatkowski, D., and Playfair, J. H. L. (1993) *Immunology* 79:138-145, Bate, C. A. W., Taverne, J., Bootsma, H. J., Mason, R. C. S. H., Skalko, N., Gregoriadis, G., and Playfair, J. H. L. (1992b) *Immunology* 76:35-41.

Berendt, A. R., Turner, G. D. H. and Newbold, C. I. (11994) *Parasitol Today* 10:412.

Clark, I. A. (1978) *Lancet* 2:75.

Clark, I. A., Virelizier, J.-L., Carswell, E. A., and Wood, P. R. (1981) *Infect. Immun.* 32:1058.

Gerold, P., Schofield, L., Brackman M., Holder, A. A., Schwarz, R. T. (1996) *Mol. Biochem. Parasitol* 75:131.

Gerold, P., Dieckman-Schuppert A. and Schwarz, R. T. (1992) Bio. Soc. Trans. 29:297.

Golgi, C. (1886) *Arch. Sci, med.* (Torino) 10:109.

Jakobsen, P. H., Morris-Jones, S. D., Hviid, L., Theander, T. G., Hoier-Madsen, M., Bayoumi, R., and Greenwood, B. M. (1993b) *Immunology* 79:653-657.

McConville, M. J. and Ferguson M. A. (1993), *Biochem. J.* 294:305.

Playfair, J. H. L. (1994) *Immunology Letters* 43:83-86.

Schofield, L., Novakovic, S., Gerold, P., Schwarz, R. T., McConville, M. J. and Tachado, S. D. (1996) *J. Immunol.* 156:1886-1896.

Schofield, L., and Hackett, F. (1993) *Journal of Experimental Medicine* 177:145-153.

Shenoy-Scaria, A. M., Kwong, J., Fujita, T., Olszowy, M. W., Shaw, A. S., and Lublin, D. M. (1992) *Journal of Immunology* 149:3535-3541.

Stefanova, I., Corcoran, M. L., Horak, E. M., Wahl, L. M., Bolen, J. B., and Horak, I. D. (1993) *Journal of Biological Chemistry* 268:20725-20728.

Stevens, V. L. (1995) *Biochem. J.* 310:361.

Tachado, S. D., Gerold, P., McConville, M. J., Baldwin, T., Quilici, D., Schwarz, R. T., and Schofield, L. (1996) *Journal of Immunology* 156:1897-1907.

Tachado, S. D., Gerold, P., Schwarz, R., Novakovic, S., McConville, M., and Schofield, L. (1997) *Proceedings of the National Academy of Sciences USA* 94:4022-4027.

Xia, M.-Q., Hale, G., Lifely, M. R., Ferguson, M. A. J., Campbell, D., Packman, L., and Waldman, H. (1993) *Biochemical Journal* 293:633-640.

The invention claimed is:

1. An isolated antibody directed against a glycosylphosphatidylinositol (GPI) molecule, wherein the isolated antibody binds to the inositolglycan domain of said GPI molecule, but is incapable of binding a GPI lipidic domain.

2. The antibody of claim 1, wherein said GPI molecule is a modified parasite GPI molecule.

3. The antibody of claim 2, wherein said parasite is *Plasmodium*.

4. The antibody of claim 3, wherein said *Plasmodium* is *P. falciparum*.

5. The antibody of claim 1, wherein said GPI inositolglycan domain comprises the structure ethanolamine-phosphate-(Manα1,2)-Manα1,2 Manα1,6 Manα1,4 GlcN-myo-inositol phosphoglycerol.

6. The antibody of claim 1, wherein said GPI inositolglycan domain comprises the structure X1-X2-X3-X4-ethanolamine-phosphate-(Manα1,2)-Manα1,2Manα1,6Manα1,4GlcN -myo-inositol phosphoglycerol wherein X1, X2, X3 and X4 are any 4 amino acids.

7. The antibody of claim 1, wherein said GPI inositolglycan domain comprises the structure
EtN-P-[Mα2]Mα2 Mα 6 Mα4Gα6Ino
EtN-P-[Mα2][G]Mα2 Mα6 Mα4Gα6Ino
EtN-P-[Mα2][X]Mα2Mα6Mα4Gα6Ino
EtN-P-[Mα2][EtN-P]Mα2Mα6 Mα4Gα6Ino
EtN-P-Mα2 Mα6 Mα4G
Mα2 Mα6 Mα4G
EtN-P-Mα2 Mα6 M
EtN-P-[Mα2][G]Mα2 Mα6 Mα4G
EtN-P-[Mα2][X]Mα2 Mα6 Mα4G
EtN-P-[Mα2][EtN-P]Mα2 Mα6 Mα4G
Mα2 [Mα2][G]Mα2 Mα6 Mα4G
Mα2 [Mα2][X]Mα2 Mα6 Mα4G
Mα2 [Mα2][EtN-P]Mα6 Mα4G
Mα6 Mα4Gα6Ino
Mα2 Mα6 Mα4Gα6Ino
Mα2 [Mα2]Mα6 Mα4Gα6Ino
Mα2 [Mα2][G]Mα6 Mα4Gα6Ino
Mα2 [Mα2][X]Mα6 Mα4Gα6Ino
EtN-P-[Mα2][G]Mα2 Mα6 M
EtN-P-[Mα2][X]Mα2 Mα6 M
EtN-P-[Mα2][EtN-P]Mα2 Mα6 M
Mα2 [Mα2][G]Mα2 Mα6 M
Mα2 [Mα2][X]Mα2 Mα6 M
Mα2 [Mα2][EtN-P]Mα6 M
Mα2 Mα6 M
Mα6 Mα4G
EtN-P-[Mα2][G]Mα2 M
EtN-P-[Mα2][X]Mα2 M
EtN-P-[Mα2][EtN-P]Mα2 M
wherein EtN is ethanolamine, P is phosphate, M is mannose, G is non-N-acetylated glucosamine, [G] is any non-N-acetylated hexosamine, Ino is inositol or inositol-phosphoglycerol, [X] is any other substitute, α represent α-linkages which may be substituted with δ-linkages wherever required, and numeric values represent positional linkages which may be substituted with any other positional linkages as required.

8. A composition comprising an antibody according to any one of claims 1 or 2-7.

* * * * *